US011459439B2

(12) United States Patent
Nash et al.

(10) Patent No.: US 11,459,439 B2
(45) Date of Patent: Oct. 4, 2022

(54) SURFACE MODIFICATION OF POLYMER FOAMS USING PLASMA

(71) Applicants: Lawrence Livermore National Security, LLC, Livermore, CA (US); The Texas A&M University System, College Station, TX (US)

(72) Inventors: Landon D. Nash, Sunnyvale, CA (US); Duncan J. Maitland, College Station, TX (US); Nicole Docherty, Trop, MI (US); Thomas S. Wilson, San Leandro, CA (US); Ward Small, IV, Livermore, CA (US); Jason Ortega, Pacifica, CA (US); Pooja Singhal, Redwood City, CA (US)

(73) Assignees: Lawrence Livermore National Security, LLC, Livermore, CA (US); The Texas A&M University System, College Station, TX (US)

(*) Notice: Subject to any disclaimer, the term of this patent is extended or adjusted under 35 U.S.C. 154(b) by 0 days.

(21) Appl. No.: 16/984,370

(22) Filed: Aug. 4, 2020

(65) Prior Publication Data

US 2020/0362134 A1 Nov. 19, 2020

Related U.S. Application Data

(63) Continuation of application No. 15/746,471, filed as application No. PCT/US2016/043657 on Jul. 22, 2016, now Pat. No. 10,781,294.

(Continued)

(51) Int. Cl.
*C08J 9/36* (2006.01)
*B29C 59/14* (2006.01)

(Continued)

(52) U.S. Cl.
CPC .......... *C08J 9/365* (2013.01); *A61L 24/0036* (2013.01); *A61L 24/046* (2013.01); *A61L 31/06* (2013.01);

(Continued)

(58) Field of Classification Search
CPC ..... C08J 2205/04; C08J 9/36; B29C 44/5663; A61L 24/0036; B32B 5/18
See application file for complete search history.

(56) References Cited

U.S. PATENT DOCUMENTS 3,175,030 A   3/1965 Geen
2007/0005140 A1  1/2007 Kim et al.

(Continued)

FOREIGN PATENT DOCUMENTS

CN    103357063    10/2013
EP    2727707      5/2014

(Continued)

OTHER PUBLICATIONS

European Patent Office, Examination Report dated Jun. 9, 2020 in European patent application No. 16 831 145.4-1107, 3 pages total.

(Continued)

*Primary Examiner* — Alexandre F Ferre
(74) *Attorney, Agent, or Firm* — Trop, Pruner & Hu, P.C.

(57) ABSTRACT

An embodiment includes a system comprising: a monolithic shape memory polymer (SMP) foam having first and second states; wherein the SMP foam includes: (a) polyurethane, (b) an inner half portion having inner reticulated cells defined by inner struts, (c) an outer half portion, having outer reticulated cells defined by outer struts, surrounding the inner portion in a plane that provides a cross-section of the SMP foam, (d) hydroxyl groups chemically bound to outer surfaces of both the inner and outer struts. Other embodiments are discussed herein.

20 Claims, 9 Drawing Sheets

Related U.S. Application Data

(60) Provisional application No. 62/196,966, filed on Jul. 25, 2015.

(51) Int. Cl.

| | | |
|---|---|---|
| *B32B 27/06* | (2006.01) | |
| *B32B 5/18* | (2006.01) | |
| *A61L 31/14* | (2006.01) | |
| *A61L 31/06* | (2006.01) | |
| *A61L 24/00* | (2006.01) | |
| *A61L 24/04* | (2006.01) | |
| *B05D 1/00* | (2006.01) | |
| *B05D 3/14* | (2006.01) | |
| *B05D 7/02* | (2006.01) | |
| *B29K 33/04* | (2006.01) | |
| *B29C 44/56* | (2006.01) | |
| *B29K 69/00* | (2006.01) | |
| *B29K 75/00* | (2006.01) | |
| *B29K 77/00* | (2006.01) | |

(52) U.S. Cl.
CPC ............. *A61L 31/14* (2013.01); *A61L 31/146* (2013.01); *B05D 1/62* (2013.01); *B05D 3/144* (2013.01); *B05D 7/02* (2013.01); *B29C 59/14* (2013.01); *B32B 5/18* (2013.01); *B32B 27/06* (2013.01); *C08J 9/36* (2013.01); *A61L 2400/16* (2013.01); *A61L 2430/36* (2013.01); *B29C 44/5663* (2013.01); *B29K 2033/04* (2013.01); *B29K 2069/00* (2013.01); *B29K 2075/00* (2013.01); *B29K 2077/00* (2013.01); *B29K 2995/0093* (2013.01); *C08J 2201/026* (2013.01); *C08J 2205/04* (2013.01); *C08J 2207/10* (2013.01); *C08J 2375/04* (2013.01)

(56) References Cited

U.S. PATENT DOCUMENTS

| | | |
|---|---|---|
| 2009/0061200 A1 | 3/2009 | Hild et al. |
| 2011/0039967 A1 | 2/2011 | Wilson et al. |
| 2012/0158034 A1 | 6/2012 | Wilson et al. |
| 2013/0253086 A1 | 9/2013 | Wilson et al. |
| 2014/0135810 A1 | 5/2014 | Divino et al. |
| 2014/0142207 A1 | 5/2014 | Singhal et al. |

FOREIGN PATENT DOCUMENTS

| | | |
|---|---|---|
| JP | 2006514129 | 4/2006 |
| JP | 2013511466 | 4/2013 |
| WO | WO2004067614 | 8/2004 |
| WO | WO2011063370 | 5/2011 |
| WO | 2014078458 A2 | 5/2014 |

OTHER PUBLICATIONS

Chinese Patent Office, Examination Report and Search Report dated Jun. 23, 2020 in Chinese patent application No. 201680024837.7, 25 pages total.
Chinese Patent Office, Office Action dated Feb. 5, 2021 in Chinese Patent Application No. 201680024837.7 (17 pages).
Japanese Patent Office, Office Action dated Sep. 1, 2020 in Japanese patent application No. 2017-557109, 9 pages total.
European Patent Office, Office Action dated Jan. 12, 2021 in European patent application No. 16 831 145.4, 4 pages total.
European Patent Office, Office Action dated Apr. 6, 2022 in European Patent Application No. 16831145.4 (5 pages).
Hearon, et al., "Electron Beam Crosslinked Polyurethane Shape Memory Polymers with Tunable Mechanical Properties", Macromolecular Chemistry and Physics, vol. 214, Jun. 1, 2013, pp. 1258-1272, Wiley-VCH Verlag GmbH And Co. KGaA, Weinheim, DE.
European Patent Office, Extended European Search Report dated Feb. 20, 2019 in European Patent Application No. 16831145.4.
The International Searching Authority, International Preliminary Report on Patentability dated Jan. 30, 2018 for International application No. PCT/US2016/043657.
European Patent Office, Communication pursuant to Article 94-3 EPC dated Feb. 5, 2020 in European Patent Application No. 16631145.4, 3 pages total.
European Patent Office, Office Action dated Oct. 1, 2019 in European patent application No. 16831145.4, 4 pages.
The International Searching Authority, Written Opinion of the International Searching Authority and the International Search Report dated Dec. 8, 2016 in International Application No. PCT/US2016/043657, 10 pages.
Nash et al., "Characterization of Plasma Deposited Hydrocarbon Diffusion Barriers for Embolic Foam Devices," Texas A&M University, College Station, Texas, US.
Akhavan et al., "Hydrophobic Plasma Polymer Coated Silica Particles for Petroleum Hydrocarbon Removal," ACS Applied Materials & Interfaces, Aug. 13, 2013, pp. 8563-8571, American Chemical Society.
Schwarz-Selinger et al., "Plasma chemical vapor deposition of hydrocarbon films: The influence of hydrocarbon source gas on the film properties," Journal of Applied Physics, Oct. 1, 1999, pp. 3988-3996, vol. 86, No. 7.
Furlan et al., "Diamond-Like Carbon Films Deposited by Hydrocarbon Plasma Sources," Reviews on Advanced Materials Sciences 34, 2013, pp. 165-172, Advanced Study Center Co. Ltd.
Siffer et al., "Alkene Pulsed Plasma Functionalized Surfaces: An Interfacial Diels-Alder Reaction Study," 2005, pp. 289-303, Wiley-VCH Verlag Gmbh & Co., KGaA, Weinheim, Germany.
Guerrouani et al., "Allylamine Plasma-Polymerization on PLLA Surface Evaluation of the Biodegradation," Journal of Applied Polymer Science, May 1, 2007, pp. 1978-1986, vol. 105, Wiley Periodicals Inc.
Barry et al., "Using Plasma Deposits to Promote Cell Population of the Porous Interior of Three-Dimensional Poly (D,L-Lactic Acid) Tissue-Engineering Scaffolds," Advanced Functional Materials, 2005, pp. 1134-1140, Wiley-VCH Verlag Gmbh & Co., KGaA, Weinheim, Germany.
Yang et al., "Enhanced cell affinity of poly (D,L-lactide) by combining plasma treatment with collagen anchorage," Biomaterials 23, 2002, pp. 2607-2614, Elsevier Science Ltd.
Dismet et al., "Nonthermal Plasma Technology as a Versatile Strategy for Polymeric Biomaterials Surface Modfication: A Review," Biomacromolecules vol. 10, No. 9, Sep. 2009, pp. 2351-2378, The American Chemical Society.
Shen et al., "Combining oxygen plasma treatment with anchorage of cationized gelatin for enhancing cell affinity of poly(lactide-co-glycolide)", Biomaterials 28, 2007, pp. 4219-4230, Elsevier Ltd.
Favia et al., "Plasma treatments and plasma deposition of polymers for biomedical applications," Surface and Coatings Technology 98, 1998, pp. 1102-1106, Elsevier Science S.A.
Wu et al., "Non-fouling surfaces produced by gas phase pulsed plasma polymerization of an ultra low molecular weight ethylene oxide containing monomer," Colloids and Surfaces B: Biointerfaces 18, 2000, pp. 235-248, Elsevier Science B.V.
Coulson et al., "Plasmachemical Functionalization of Solid Surfaces with Low Surface Energy Perfluorocarbon Chains," Langmuir vol. 16, No. 15, 2000, pp. 6287-6293, American Chemical Society.
Coulson et al., "Super-Repellent Composite Fluoropolymer Surfaces," Journal of Physical Chemistry B vol. 104, No. 37, 2000, pp. 8836-8840, American Chemical Society.
Coulson et al., "Ultralow Surface Energy Plasma Polymer Films," Chemical Materials vol. 12, No. 7, 2000, pp. 2031-2038, American Chemical Society.
Moss et al., "Plasma Oxidation of Polymers," Plasma Chemistry and Plasma Processing vol. 6, No. 4, 1986, pp. 401-415, Plenum Publishing Corporation.
De Nardo et al., "Shape memory polymer foams for cerebral aneurysm reparation: Effects of plasma sterlization on physical

(56) References Cited

OTHER PUBLICATIONS properties and cytocompatibility," Acta Biomaterialia 5, Dec. 13, 2008, pp. 1508-1518, Elsevier Ltd.

Sanchis et al., "Surface Modification of a Polyurethane Film by Low Pressure Glow Discharge Oxygen Plasma Treatment," Journal of Applied Polymer Science vol. 105, Apr. 9, 2007, pp. 1077-1085, Wiley Periodicals, Inc.

Lerouge et al., "Plasma Sterilization: A Review of Parameters, Mechanisms and Limitations," Plasmas and Polymers vol. 6, No. 3, Sep. 2001, pp. 175-188, Plenum Publishing Corporation.

Tatoulian et al., "Plasma Surface Modification of Organic Materials: Comparison between Polyethylene Films and Octadecyltrichlorosilane Self-Assembled Monolayers," Langmuir vol. 20, No. 24, Oct. 29, 2004, pp. 10481-10489, American Chemical Society.

Von Keudell et al., "Surface relaxation during plasma-enhanced chemical vapor deposition of hydrocarbon films, investigated by in situ ellipsometry," Journal of Applied Physics vol. 81, No. 3, Feb. 1, 1997, pp. 1531-1535, AIP Publishing.

Chu et al., "Plasma-surface modification of biomaterials," Materials Science and Engineering R 36, 2002, pp. 143-206, Elsevier Science B.V.

Singhal et al., "Ultra Low Density and Highly Crosslinked Biocompatible Shape Memory Polyurethane Foams," Journal of Polymer Science Part B: Polymer Physics, vol. 50, No. 10, 2012, pp. 724-737, Wiley Periodicals, Inc.

Singhal et al., "Controlling the Actuation Rate of Low-Density Shape-Memory Polymer Foams in Water," Macromolecular Chemistry and Physics, Macromolecular Journals, vol. 214, No. 11, 2013, pp. 1204-1214, Wiley-VCH Verlag GmbH & Co., KGaA, Weinheim.

SURFACE MODIFICATION OF POLYMER FOAMS USING PLASMA

PRIORITY CLAIM

This application is a continuation of U.S. patent application Ser. No. 15/746,471, filed Jan. 22, 2018, which is a § 371 national stage of international application PCT/US2016/043657, which filed Jul. 22, 2016, which claims priority to U.S. Provisional Patent Application No. 62/196,966 filed on Jul. 25, 2015 and entitled "Reticulation and Surface Modification of Polymer Foams Using Plasma." The content of each of the above applications is hereby incorporated by reference

FEDERALLY SPONSORED RESEARCH AND DEVELOPMENT

This invention was made with government support under R01EB000462 awarded by National Institutes of Health, National Institute of Biomedical Imaging and Bioengineering. The government has certain rights in the invention. Furthermore, the United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

The current standard for preventing hemorrhagic stroke involves treating intracranial aneurysms with bare platinum coils, which are delivered through a microcatheter and left within the aneurysm to initiate a clotting response. Bare platinum coils have helped to reduce the annual number of hemorrhagic stokes in the United States to approximately 103,000, but this treatment still has clinical limitations. For example, volumetric filling densities that are considered to be very high by clinical standards (30-35%) still do not cause complete embolization. Attempts to increase packing density with more coils can lead to over packing and eventual aneurysm rupture. Embolizations that are initially effective can still have recanalization rates as high as 35% and 50% in large and giant aneurysms, respectively. Additionally, bare platinum coils are cost prohibitive when treating large aneurysms. This cost is associated with the number of implanted coils, as well as increased procedure time and complexity. Thus, the cost and efficacy limitations of bare platinum GDCs demand solutions for more efficient volumetric filling of cranial aneurysms.

Low density shape memory polymer (SMP) embolic foams have been proposed as a solution to alleviate the drawbacks associated with current embolization therapies. Low density SMP foams can be compressed to fractions of their expanded volume, allowing them to be delivered through a micro catheter. After implantation, a stimulus, such as heat, can restore the low profile foam to its original expanded geometry. Incorporating these low density SMP foams with current coiling techniques can significantly reduce the number of coils necessary to fill an aneurysm, which also reduces procedure time and cost. Similar to other coil embolization devices, the embolic foam occludes the aneurysm by disrupting blood flow and causing a clot to form within the aneurysm volume. Recent results reported demonstrate promising biocompatibility for bulk SMP foams implanted in a porcine vein pouch aneurysm model. The volumetric expansion capabilities and demonstrated biocompatibility of SMP foams make them a promising solution for providing more effective embolization and improved healing. However, additional work is needed for the effective delivery and actuation of these foams for commercial medical applications.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

DETAILED DESCRIPTION

Figure 1:
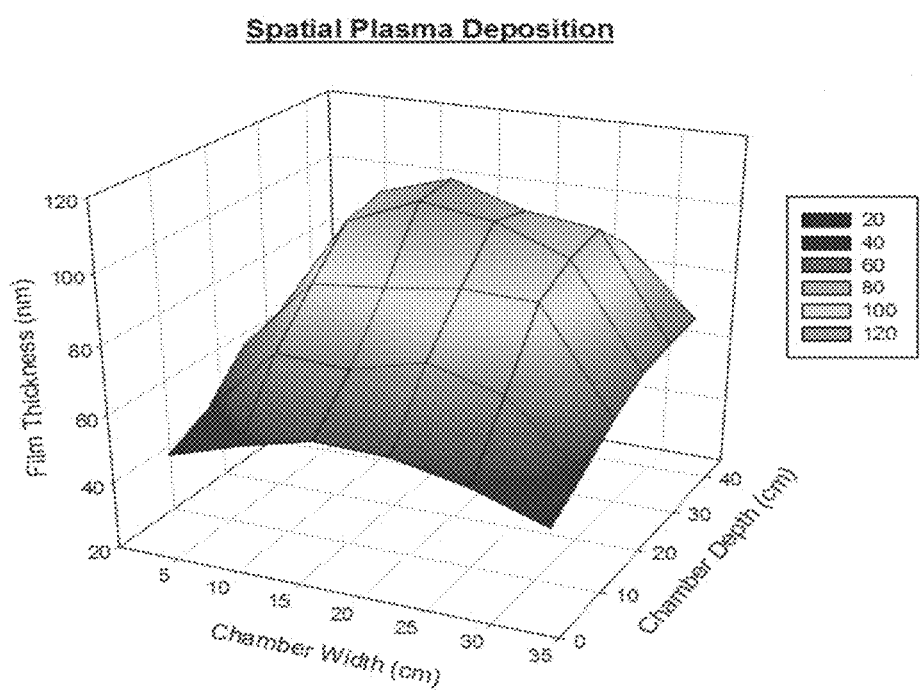
FIG. 1 includes ellipsometry for an embodiment measured spatial deposition map for a 6×6 grid silicon wafers raised on glass cuvettes and treated with process LEA at 150 watts for 7.5 minutes.

Reference will now be made to the drawings wherein like structures may be provided with like suffix reference designations. In order to show the structures of various embodiments more clearly, the drawings included herein are diagrammatic representations of structures. Thus, the actual appearance of the structures, for example in a photomicrograph, may appear different while still incorporating the claimed structures of the illustrated embodiments. Moreover, the drawings may only show the structures useful to understand the illustrated embodiments. Additional structures known in the art may not have been included to maintain the clarity of the drawings. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements co-operate or interact with each other, but they may or may not be in direct physical or electrical contact.

Applicant determined a major hurdle for the commercialization of aneurysm filling SMP embolic foams is the concept of working time, which is the window of time a physician has to deliver an SMP device through a microcatheter, reposition the device in the aneurysm, or retract the device before it has expanded sufficiently to bind in the catheter. Applicant determined bulk material modifications (e.g., changing the chemistry within the struts of a form as opposed to adding a surface treatment to the form struts) have successfully delayed or prevented form expansion at body temperature by increasing the material hydrophobicity or rigidity of the polymer backbone. However, Applicant further determined these bulk modifications simply change the linear expansion rate, which requires concessions for ultimate device expansion or a working time that is at the clinical minimum (approximately 5 minutes). Applicant determined in some embodiments the form would ideally actuate in a non-linear fashion where the device expands a few thousands of an inch over approximately 10 minutes, and subsequently recover 20-30 thousandths in the next 20 minutes. This expansion profile would enable clinically relevant SMP devices for treating neurovascular aneurysms. A hydrocarbon surface diffusion barrier deposited using plasma enhanced chemical vapor deposition (PECVD) is proposed in embodiments described herein to achieve this nonlinear expansion behavior by delaying the moisture plasticization rate of the SMP foam without mechanically constraining the form Despite a wide variety of plasma induced biomaterial surfaces, a plasma approach has not been proposed to delay the moisture plasticization rate of SMP polyurethane forms.

Implanted SMP foam is meant to serve as a tissue scaffold for thrombus formation and subsequent cellular healing. However, gas blown forms inherently have membranes between pores, leading to limitations as tissue scaffolds. Reticulation, or the removal of membranes between adjacent form pores, would be advantageous for increasing the permeability of the form and improved tissue scaffolding by creating interconnected porosity. When form is exposed to fluid flow, fully interconnected pores enable increased fluid permeability into the full volume of the material, abnormal fluid shear rates, and longer fluid residence times. These fluid phenomena make reticulated foams excellent candidates for embolic applications because they promote rapid blood coagulation in vivo, and allow for cellular infiltration during the healing response. Controlled reticulation of SMP foam would have multiple thrombogenic benefits, such as an optimized surface to volume ratio for blood coagulation triggered through the intrinsic pathway and flow stagnation within the form, which leads to thrombogenic fluid shear rates. Additionally, a reticulated foam would allow for cellular infiltration as the body heals the thrombus within the form.

Applicant determined traditional reticulation processes (e.g., chemical etching/leaching, oxidation, quenching, oxidation, zapping, pressurized air, and controlled combustion/concussion) are too aggressive to use with ultra-low density shape memory polymers (defined herein). Techniques such as acid etching and zapping destroy the mechanical integrity of the form.

Applicant has determined a plasma approach can be employed to non-thermally degrade and volatize the surface of an SMP foam using a reactive oxygen and tetra-flouromethane plasma. This approach results in reticulation because the membranes have a higher surface area to volume ratio than the form struts. Applicant further determined low pressure/temperature plasma processes, which are far more conducive to treating polymers when compared to typical plasma membrane processes that occur at temperatures ranging from hundreds to thousands of degrees Celsius, require uncommon specialized equipment. Fine control over plasma parameters such as sample placement, masking, power, duration, and plasma atmospheric gases all contribute to specified control over spatial reticulation and functionalization. Expanded surface function capabilities (as included in embodiments described herein) would allow for numerous novel applications in medicine, such as drug delivery, as well in commercial industries.

The optimization of cold plasma surface functionalization and spatially controlled reticulation of polymer forms (described in embodiments included herein) allows for a range of applications (including but not limited to) filtration, absorption, detection, blooding clotting, tissue scaffolding, and drug delivery. Plasma reticulation process parameters are finely tuned in order to achieve such applications. Control of the permeation of surrounding media across form, the residence time of the surrounding media in the form, and the control over the variation in mechanical properties allow for such broad applications of form polymers.

In some embodiments, the plasma based functionalization of the polymer surface may be characterized as passive, semi-active, or active, where the range of applications may include (but is not limited to) filtration, absorption, detection, water diffusion barriers, and drug delivery. A passive surface functionalization may be characterized by the modification of a basic surface property such as (but not limited to) hydrophobicity, or conductivity. A semi-active surface functionalization may be characterized by the form actively interacting with the surrounding media leading to preferential absorption, adsorption/retention of specific chemical or biologic moieties. An active surface functionalization goes beyond mere interaction with the surrounding media in that an active surface functionalization allows the polymer form surface to actively interact with the surrounding media and change its own behavior as a result including (but not limited to) fluorescence, change in pH, change in color, or to serve as a reactive substrate for the addition of surface additives such as (but not limited to) x-ray contrast agents.

In embodiments, unsaturated hydrocarbon gasses including acetylene, ethylene, and propylene are used to deposit an aliphatic water diffusion barrier to slow the moisture plasticization rate of SMP foams and delay passive form expansion in vitro. By altering the bulk hydrophobicity of the form (i.e., changing chemistry within the strut itself) and the diffusion characteristics of the surface (not within the strut but the surface of the strut), the actuation profile of the form can be tailored for delayed expansion in body temperature water.

In an embodiment, the degree of reticulation across the form thickness is controlled in order to control the permeability of the surrounding media in the form, as well as its residence time in the material. This can be employed in a variety of applications where time is a governing factor in the interaction of polymer and surrounding media, such as in applications of detection, filtration, absorption, blood clotting, tissue scaffolding and drug delivery. On exposure to the radicals in the plasma, polymer chains are oxidized and begin to break down into smaller fragments, a phenomenon that progresses further with continued exposure. Ultimately, these fragments become small enough that they can get volatilized, leading to removal of the material. In other words, it is effectively a controlled oxidation (or controlled burning) process. As the residual cell membranes have a high surface area and much lower thickness compared to cell struts, they get volatilized first, leaving a reticulated cell structure behind. Further, an ultra-low density form limits the dampening of the plasma energy, resulting in good reticulation depths via the claimed process.

In an embodiment a reticulated foam is in an aneurysm treatment device. A reticulation gradient can help control the rate of permeation of the blood through the form. Further modulating spatial permeability and can also vary the rate and volume of blood clot in the device, potentially leading to control over the physiological response of the material.

An embodiment is directed to functionalization of the form surface using plasma, which is aimed at achieving a range of passive, semi-active and active surface modifications that may assist in various end applications such as filtration, absorption, detection and drug release.

The process of functionalization of the form surface is divided into three categories: (a) Inactive/Passive functionalizations; (b) Semi-active functionalizations; and (c) Active functionalizations.

Inactive functionalizations include surface modifications that change the surface behavior of the material and change how it reacts with the environment in a passive manner (e.g. changes in hydrophilicity, conductivity, etc.) Plasma surface modification using hydrocarbon process gases such as acetylene, ethylene, propylene, methane, ethane, propane, or butane can create a hydrophobic material surface. This surface creates a moisture diffusion barrier and delays the infiltration of water into the polymer network when SMP foam is immersed in an aqueous environment. This diffusion barrier can be tailored to affect the diffusion driven process of moisture plasticized Tg depression. If the plasticized Tg of the form eventually falls below body temperature, the diffusion barrier can be optimized to create delayed passive expansion profiles in vivo. This approach increases the utility of SMP foam in catheter based medical devices because it increases the working time of the device while eliminating the need for an external heat source.

Plasma surface modification with argon, oxygen, or tetraflouromethane process gases can result in large amounts of surface hydroxyl groups on the SMP surface. These groups serve as reactive sites to bind other molecules to the SMP surface. For example, the treated SMP foam can be soaked in an anhydrous solution of organic solvent and diisocyanate to create reactive surface "tethers" terminated with an isocyanate group. Subsequently, immersing the sample in an organic solution with hydroxyl terminated compounds to covalently bind compounds to the material surface.

Semi-active functionalizations include surface modifications that change the surface behavior of the material so it can interact actively with the environment. Surface modifications that enable absorption of a desired analyte from its immediate environment (possibly by means of chemical bonding), or provide enhanced adhesion of specific molecular entities can be classified under this category. Such modifications can find application in areas such as filtration, or removal of specific particulates/pathogens/molecules from the ambient air or fluid. With controlled variation in the permeability of the material to fluid/gas media by virtue of morphology variations, we can effectively control the residence time of the media as desired for efficient absorption/detection.

In biomedical applications, a range of therapeutic drugs can be conjugated onto the polymer surface for passive diffusion, through the use of inactive functionalization, or environmentally stimulated active release in the surrounding area, through the use of semi-active functionalization, for an improved healing response. For example, an acetylene plasma could be optimized to deposit a hydrocarbon film with reactive vinyl groups. These vinyl groups can be reacted with thiol terminated cysteine groups to conjugate proteins or peptides to the material surface. This thiolene reaction may be initiated with UV light and/or heat.

Active functionalizations may be defined as functional groups on the polymer surface that absorb specific particulates/pathogens/molecules and undergo a specific change in themselves that indicates the detection of such entities in the environment (e.g. the material may fluoresce or indicate change in pH, or simply change color on interaction with specific entities).

In an embodiment a platinum 1, 2-enedithiolate complex with an appended alcohol is conjugated to the polymer surface to achieve active functionalization. This molecule is converted to a room temperature lumiphore upon exposure to selected phosphate esters. Ultra-low density shape memory forms functionalized with this molecule serves as a high efficiency platform for organo-phosphate detector technology. This technology facilitates rapid detection of volatile fluoro and cyano phosphates, which form major constituents of the chemical warfare arsenal.

Embodiments are directed towards treating polymeric devices with a plasma surface treatment system similar to the Aurora 350 Plasma Surface Treatment System manufactured by Plasma Technology Systems. This particular plasma system does not employ traditional vacuum pumps with hydrocarbon oil lubricants, and instead uses fomblinized, passivated halocarbon oil vacuum pumps that have few stipulations for pumping flammable or highly oxidative atmospheres. Forms are exposed to a variety of process gasses at set flow rates of 5-1000 sccm and under vacuum at 5-500 mTorr in the system. Once equilibrated the ambient atmosphere is ionized into a plasma using RF electrodes of 1-1000 W. The polymer surface is chemically modified without causing thermal damage to the sample by this highly reactive plasma atmosphere. The spatial variation and composition of the surface modification is controlled by process parameters, process gasses, sample orientation, sample masking, and sample shielding. The process may or may not use physical or chemical masking. All of these properties may be optimized in order to achieve control over the spatial variation, or to introduce a gradient in the degree of reticulation of the form. Spatially controlled reticulation allows for anisotropic mechanical properties useful for controlled vascular embolization, tissue engineering, or commercial applications such as light weight shock absorbing helmets and filtration.

In an embodiment surface functionalization of shape memory polymer (SMP) foams enables applications for controlled form expansion rates in physiologic environments, molecular sensing, drug delivery, and provides reactive sites for grafting of other reactive agents to the polymer surface.

In an embodiment where time is a governing factor in the interaction of the polymer and the surrounding media, such as applications of detection, filtration, absorption, blood clotting, and drug delivery, control over the degree of reticulation with possible spatial gradient and/or the mechanical properties of the material may be utilized in order to control the permeability of the surrounding media as well as its residence time in the material.

An embodiment is directed to utilizing a reticulation gradient in order to control the rate of permeation of the blood through the form in an aneurysm device. Spatial permeability can also vary the rate and area of blood clot in the device, potentially leading to control over the physiological response of the material.

Another embodiment may exercise control over the mechanical properties, such as modulus or recovery stresses of the material directed towards various applications such as shock-absorption in light-weight helmets to minimize impact injury.

A further embodiment is directed to a method of functionalization of the form surface using plasma surface modification, aimed at achieving a range of passive, semi-active, and active surface modifications that may assist in various end applications such as filtration, absorption, detection, and drug release.

An embodiment is directed to a method of plasma surface modifications resulting in semi-active functionalizations. These semi-active functionalizations modify the surface behavior of the material so that it can interact actively with the environment. This may include surface modifications that enable absorption of a desired analyte from its immediate environment through chemical bonding or other means, or provide enhanced adhesion of specific molecular entities.

Another embodiment is directed to a method of plasma surface modifications resulting in a range of therapeutic drugs conjugated onto the polymer surface for passive diffusion.

Another embodiment is directed to a method of plasma surface modifications resulting in environmentally stimulated release in the surrounding area, including, but not limited to modifications that improve the healing response.

An embodiment is directed to a method of plasma surface modifications resulting in active functionalizations, where active functionalizations are defined as functional groups on the polymer surface that absorbs specific particulates/pathogens/molecules and undergo a specific change in themselves that indicates the detection of such entities in the environment.

An embodiment is directed to a method of plasma surface modifications resulting in an active functionalization where the material may fluoresce, indicate a change in pH, or simply change color on interaction with specific entities.

Another embodiment is directed to a method of plasma surface modifications resulting in an active functionalization characterized by its active functionalization that enables the rapid detection of volatile fluoro and cyano phosphates, which form major constituents of the chemical warfare arsenal. A platinum 1,2-enedithiolate complex with an appended alcohol can be conjugated to the polymer surface to achieve active functionalization. The molecule is converted to a room temperature lumiphore upon exposure to selected phosphate esters allowing the shape memory form to function as a high efficiency platform for organ-phosphate detector technology.

Working Example 1

Methods

Plasma Gas Composition

This study focused on characterizing the functional relationship between process parameters and the characteristics of the resulting plasma deposited film. Process gas compositions and room temperature chamber pressures prior to plasma ignition are summarized in Table I. Plasma gas compositions were run on silicon wafers at four time intervals between 1 and 30 minutes at the discreet powers of 75, 150, 225, and 300 Watts for a total 128 different process combinations.

TABLE I

PLASMA GAS COMPOSITIONS AND FLOW RATES

| Process Label[a] | Process Conditions | | | |
|---|---|---|---|---|
| | Ethylene Flow Rate (sccm) | Propylene Flow Rate (sccm) | Acetylene Flow Rate (sccm) | Average Process Pressure (mTorr) |
| LE | 150 | — | — | 77 |
| LEA | 125 | — | 25 | 77 |
| HE | 300 | — | — | 125 |
| HEA | 250 | — | 50 | 125 |
| LP | — | 150 | — | 70 |
| LPA | — | 125 | 25 | 74 |
| HP | — | 300 | — | 119 |
| HPA | — | 250 | 50 | 119 |

[a]LE—Low flow ethylene, LEA—Low flow ethylene/acetylene, HE—High flow ethylene, HEA—High flow ethylene/acetylene, LP—Low flow propylene, LPA—Low flow propylene/acetylene, HP—High flow propylene, HPA—High flow propylene/acetylene. Process flow rate in standard cubic centimeters (sccm)

Sample Preparation

Silicon wafers (University Wafer, Inc.) were cut into rectangles approximately 1.25 cm×1.7 cm, cleaned in water and isopropanol under sonication for 15 minutes each, dried overnight at 1 Torr, and stored under desiccation.

All SMP polyurethane forms were fabricated with a 33:67 hydroxyl equivalent ratio of triethanolamine (TEA) to N,N,N',N'-tetrakis(2-hydroxypropyl)ethylenediamine (HPED). Forms used for differential scanning calorimetry (DSC) were made with an isocyanate composition of 100 percent hexamethylene diisocyanate (HDI). Two additional form compositions were synthesized for expansion studies using a 50:50 isocyanate ratio of HDI to trimethylhexamethylene diisocyanate (TM). Based on results from a concurrent study, 3 weight percent nanoparticulate tungsten was included in one synthesis and the other included 1 weight percent nanoparticulate aluminum oxide. After synthesis, all forms were cut into 1.5×1.5×4 cm blocks and cleaned in vials using 15 minute sonication intervals. The first interval used reverse osmosis filtered water, followed by 2 intervals of isopropyl alcohol, and 4 intervals of reverse osmosis water. The cleaned forms were frozen, lyophilized, and stored under desiccation.

Cleaned forms were punched into 1 mm diameter, 4 cm long cylinders using a biopsy punch and threaded axially over a 150 micron (0.006") diameter stainless steel wire. Forms intended for expansion studies were then transferred to 0.006" diameter 92/8 Pt/W coils (Motion Dynamics) with a 0.002" diameter propylene suture threaded through the lumen. Form-over-wire (FOW) samples and form-over-coil (FOC) samples were plasma treated while suspended between two 4.5 cm tall glass cuvettes. 100HDI FOW samples were used for differential scanning calorimetry. 50TM FOC samples were compressed using an SC250 Stent Crimper (Machine Solutions Inc.) after plasma treatment. FOC samples were loaded into the crimper at 100° C., equilibrated for 15 minutes, compressed to an average diameter of 305 microns (0.012"), and held compressed during a convective air cooling cycle over a one hour period. Once at room temperature, the samples were removed and stored under desiccation.

Plasma Treatment

Plasma films were deposited using an Aurora 0350 Plasma Surface Treatment System (Plasma Technology Systems). The reaction chamber held a single glass shelf mounted in the third rack space from the bottom of the reaction chamber. For mapping the spatial reactivity of the plasma field, silicon wafers were fixed to 4.5 cm tall glass cuvettes placed in a 6×6 grid on the glass shelf. All other experiment samples were fixed to the top of a 4.5 cm tall glass cuvette centered in the back third of the shelf. The chamber was evacuated to a base pressure of 10 mTorr, followed by process gas introduction into the chamber at the specified process flow rate for 1 minute prior to plasma ignition. The plasma field was generated using a continuous 13.56 MHz RF power supply and the process gasses continued flowing through the chamber for 1 minute after plasma treatment. The chamber was then purged with atmospheric air for 10 minutes and returned to atmospheric pressure. All samples were stored in polypropylene bags or trays under desiccation.

Ellipsometry

Ellipsometric thicknesses were measured using an Alpha-SE Spectroscopic Ellipsometer (J.A. Woollam Co.) operating at 380-890 nm and a 70° angle of incidence. Data analysis employed a J.A. Woollam optical model assuming a thin transparent film on a Silicon substrate.

Contact Angle

Static water contact angle measurements were made with a CAM 200 Goniometer (KSV Instruments) using drop volumes of 5 microliters. Six contact angles were measured for each reported process using a Young/Laplace fitting model.

X Ray Photoelectron Spectroscopy (XPS)

Silicon wafers were treated with LP and LPA processes for XPS analysis. Plasma treatment times were chosen to deposit a normalized film thickness of 30 nm for each process. XPS spectra were acquired using an Omicron ESCA+ system with a Mg X ray source and CN10 charge neutralizer. XPS power, step, pass energy. Atomic ratios were calculated using the software Casa XPS.

Differential Scanning Calorimetry (DSC)

Polymer glass transition temperatures (Tg) were determined using a Q200 DSC (TA Instruments). For dry Tg, a 1-3 mg sample was loaded into a vented aluminum pan at room temperature, cooled to −40° C., and run through a heat/cool/heat cycle from −40° C. to 120° C. at temperature rates of 10° C./min. The transition inflection point during the second heat cycle was used as an estimate for Tg. For wet Tg analysis, form over wire samples were immersed in a 52° C. water bath for 5 minutes and subsequently compressed between laboratory grade kimwipe sheets (Kimberly-Clark Inc.) at 1 metric ton for 30 seconds using a #3925 Hydraulic press (Carver, Inc). The form was then loaded into a vented aluminum pan, cooled to −40° C., and heated to 80° C. at 10° C./min. Wet Tg was estimated as the heating cycle transition inflection point. Wet and Dry Tg's were measured for 5 samples of each reported plasma composition.

Form Expansion

Compressed form over wire diameters were measured with a stereoscopic microscope (Leica KL 2500 LCD). Form over wire samples were held in the same plane as a 12 mm geometric standard using a custom aluminum fixture. The fixture was submerged in a 37° C. water bath and imaged from above at 30 sec intervals for 30 minutes. Five diameter measurements were taken along the length of each form sample within the captured images using ImageJ. 3 samples of each plasma composition were measured.

Results

Process parameters including sample location within the plasma field, RF power, gas composition, pressure, and treatment time were systematically evaluated to determine their effects on film deposition rate and hydrophobicity. Select plasma processes were then applied to a clinically relevant embolic device to determine their effects on the moisture plasticization and subsequent actuation rate of SMP foam.

Spatial Plasma Reactivity

As seen in FIG. 1, the plasma deposition rate increases towards the back of the plasma chamber, except for a low reactivity margin around the periphery of the shelf. This reactivity gradient is in parallel with the flow of process gasses through the chamber. Thus, the deposition profile increases as gaseous species are exposed to the RF field for longer periods of time, increasing their reactivity. To mitigate variations due to sample placement within the chamber, all subsequent samples were fixed within the 100-120 nm deposition region shown in FIG. 1.

Hydrocarbon Film Deposition

Figures 2A, 2B:
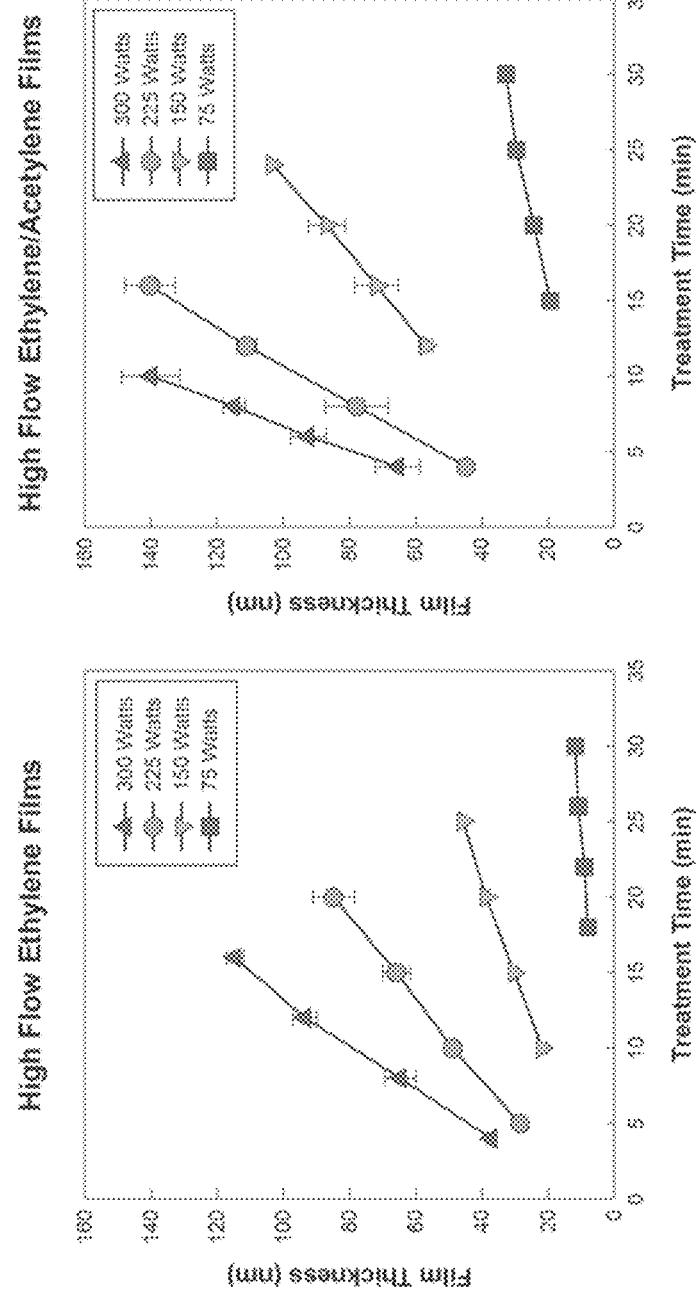
FIGS. 2A and 2B include plasma film deposition profiles for silicon wafers treated with HE processes (FIG. 2A) and HEA processes (FIG. 2B) as measured by spectroscopic ellipsometry. Error bars are MSE values for the optical model fit.

Film deposition profiles were measured to determine deposition rate for each plasma process. The graphs in FIGS. 2(A) and 2(B) depict typical deposition profiles for high flow ethylene (HE) and high flow ethylene/acetylene (HEA) processes. All processes show linear time dependent deposition profiles. The average $R^2$ value for all 32 linear regressions is 0.992. Deposition rates increased with increasing power, and with the introduction of acetylene (i.e., HEA) at similar process conditions.

Figures 3A, 3B:
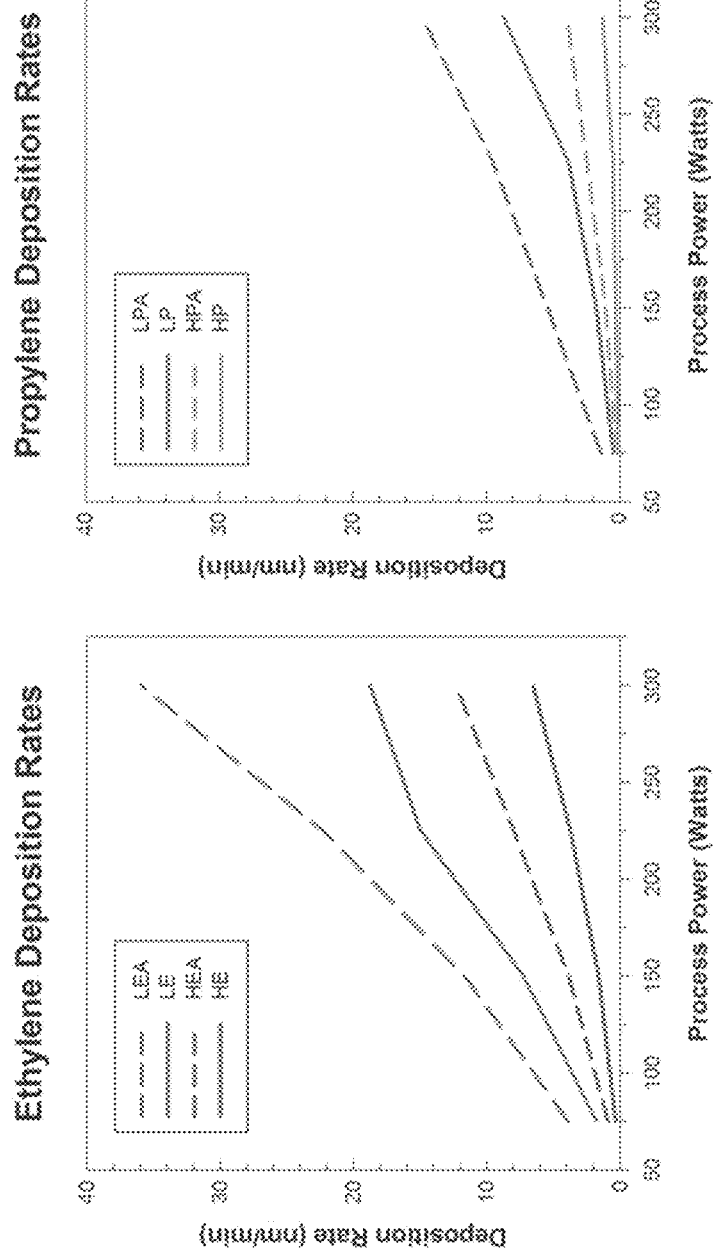
FIGS. 3A and 3B include plasma film deposition rates for ethylene processes (FIG. 3A) and propylene processes (FIG. 3B). Deposition rate was assumed to be the slope of the linear fit for each time dependent deposition profile for a given process.

FIGS. 3(A) and (B) summarize the deposition rates determined from all 128 processes. The power dependent change in deposition rate is assumed to be linear over the studied power range and the average linear $R^2$ value for all 8 plots in FIGS. 3(A) and (B) is 0.960. Increasing process power, decreasing process pressure, and introducing acetylene to a process all result in an increased deposition rate. In general, ethylene processes have faster deposition rates than propylene.

Film Hydrophobicity

Figure 4A:
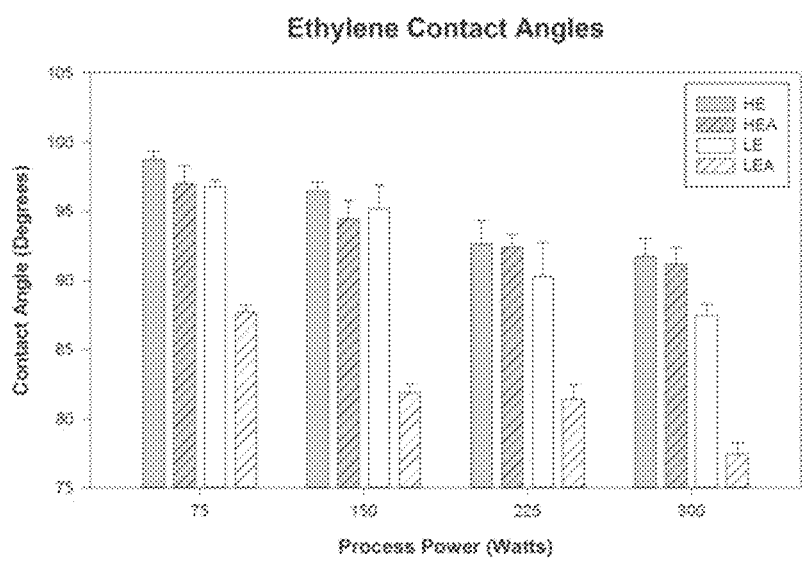
FIGS. 4A and 4B include static water contact angles on silicon wafers treated with ethylene processes (FIG. 4A) and propylene processes (FIG. 4B). Untreated silicon wafers had contact angles of 37±1° (not shown). Error bars are standard deviation (n=6).
Figure 4B:
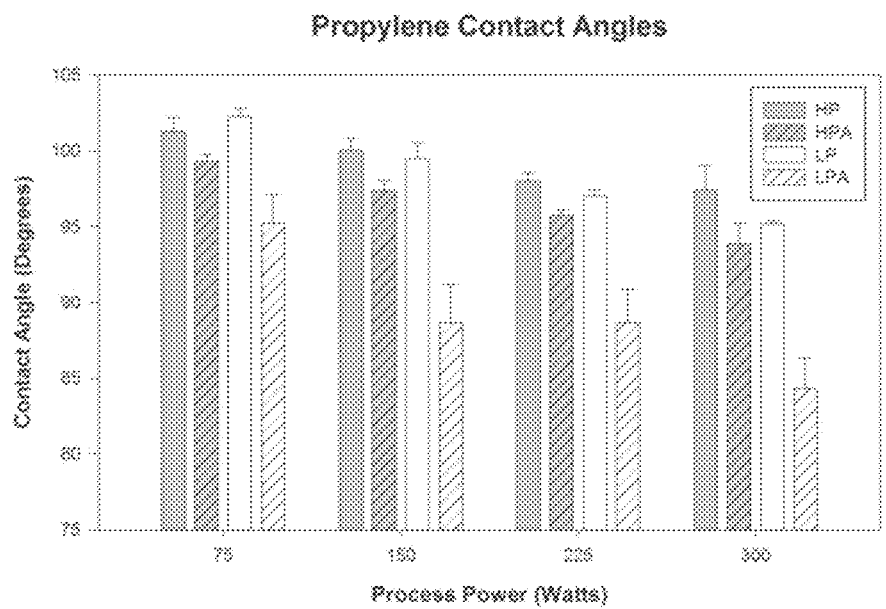

Static water contact angles for each process gas and power combination are summarized in FIGS. 4(A) and (B). Contact angle decreased with increasing process power and when introducing acetylene to a process. Propylene processes were consistently more hydrophobic than ethylene processes, presumably from methyl groups incorporated within the film. In general, process parameters that increased film deposition rate tended to decrease surface hydrophobicity. All plasma deposited films were significantly more hydrophobic than untreated silicon wafers, which had an average contact angle of 37±1° C.

Selected processes were chosen for XPS analysis to determine the power dependent changes in contact angle. All films were normalized to an average thickness of 30.5±1.5 nm. Increasing process powers resulted in higher rates of film oxidation, which contribute to lower water contact angles. This oxidation is likely due to residual radicals from higher energy processes reacting with atmospheric oxygen after plasma polymerization. Similarly, the higher reactivity of the acetylene processes likely result in higher levels of residual radicals that oxidize after plasma treatment.

Effects on Glass Transition

Four plasma processes were chosen to encompass a variety of process powers, gas compositions, pressures, and range of surface hydrophobicity. These processes were applied to the 100HDI forms at a normalized thickness of 20 nm. The dry and moisture saturated glass transition temperatures for these foams are summarized in Table II.

None of the four processes had a significant effect on the thermal properties of dry SMP foams. The glass transitions of moisture saturated SMP foams were marginally increased by the diffusion barriers. This suggests that the bulk polymer thermal properties are preserved, and any changes in form expansion rate would largely be due to the surface polymerized films modulating the rate of moisture plasticization.

TABLE II

GLASS TRANSITION TEMPERATURES (N = 5)

| Process Label[a] | Contact Angle (Degrees) | Dry $T_g$ (° C.) | Wet $T_g$ (° C.) |
| --- | --- | --- | --- |
| Untreated | 72.8 ± 0.8 | 70.0 ± 0.5 | 14.7 ± 0.7 |
| LEA75 | 88 ± 0.5 | 70.1 ± 0.4 | 17.1 ± 0.7 |
| LE225 | 90 ± 2.5 | 70.1 ± 0.4 | 15.6 ± 1.0 |
| HE300 | 92 ± 1.3 | 69.7 ± 0.5 | 17.1 ± 0.7 |
| LP75 | 102 ± 0.6 | 70.1 ± 0.3 | 16.8 ± 0.8 |

[a]Label numbers indicate process power

Effects on Expansion Rate

Figures 5A, 5B:
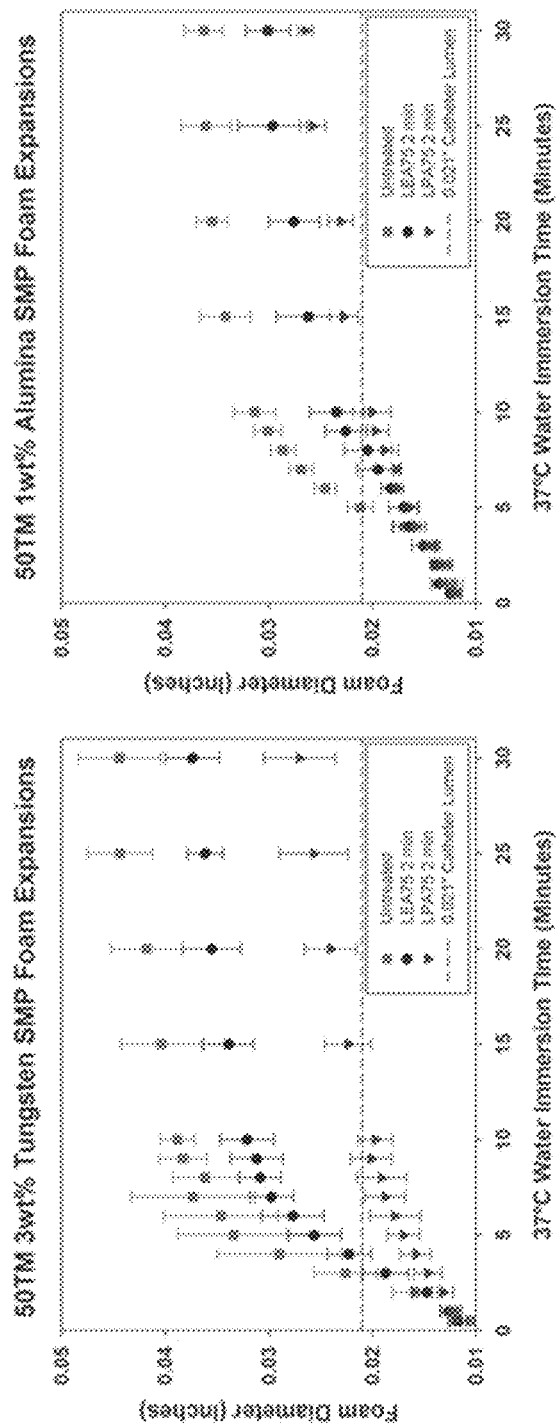
FIGS. 5A and 5B include unconstrained expansion profiles for untreated and plasma treated SMP foams doped with tungsten (FIG. 5A) and alumina (FIG. 5B) nanoparticulates. Working time is determined by the standard deviation intercept with the dotted line representing a 0.021" lumen microcatheter.

FIGS. 5(A) and (B) summarize in-vitro form expansion for two different plasma processes when compared to untreated forms. Working time is assumed to be the standard deviation intercept with the dotted line, which represents the lumen of a traditional 0.021" microcatheter used to deliver neurovascular coils.

The working time for untreated tungsten doped form is between 2 and 3 minutes (FIG. 5A). The ethylene plasma treatment (LEA75) marginally extended this working time to between 3 and 4 minutes. Both of these working times are unacceptable for the clinical environment. With a working time between 7 and 8 minutes, the propylene plasma process (LPA75) effectively tripled the working time of untreated tungsten doped form and enabled clinically relevant SMP foam performance.

When considering alumina doped forms, the working time for untreated form is between 4 and 5 minutes (FIG. 5B). Ethylene plasma treatment (LEA75) successfully extended working time above the clinical threshold to between 6 and 7 minutes. Propylene treated (LPA75) alumina doped forms had the longest working times between 9 and 10 minutes. This device performance is well within the therapeutic range for safely delivering an embolic coil, including a clinical safety factor.

Similar to bulk approaches for delaying SMP foam expansion, the observed increases in working time come at the expense of ultimate expanded diameter. Maximum expansions were determined after 30 minutes of immersion because it is estimated that acute clot formation will limit further expansion on this time scale. Untreated tungsten doped form recovered to an average diameter of 0.044" compared to 0.037" and 0.027" for LEA75 and LPA75 treated forms, respectively. Control alumina doped form recovered to an average diameter of 0.036" compared to 0.030" and 0.026" for LEA75 and LPA75 treated forms, respectively.

Although decreases in ultimate expansion limit the potential volumetric occlusion for each device, the smallest reported ultimate form diameter of 0.026" provides more volumetric occlusion and surface area through a smaller catheter lumen than the largest marketed bare platinum neurovascular coils. This expanded diameter also provides similar volumetric filling with a higher surface area when compared to 0.027" expanded diameter hydrogel coated HES-14 coils delivered through 0.019" ID microcatheters. Finally, LEA75 treated alumina forms had comparable ultimate expansion on a similar 5 minute time scale to 0.033" expanded diameter hydrogel coated HES-18 coils delivered through 0.021" ID catheters.

In an embodiment membrane removal (reticulation using an oxygen/tetrafluoromethane plasma process) from a shape memory polymer form using an oxygen/tetrafluoromethane plasma process allows for strut geometries to be conserved. Polymer films with the same composition as the SMP foam were treated with a plasma reticulation process and tested using static water contact angles. Lower contact angle infers increased hydrophilicity due to material surface oxidation.

Working Example 2

Methods

Sample Preparation

SMP foams were prepared according to the protocol described by Singhal et al (Controlling the Actuation Rate of Low-Density Shape-Memory Polymer Foams in Water; Macromol. Chem. Phys. 2013, 214, 1204-1214). with an isocyanate composition of 100 mol % trimethylhexamethylene diisocyanate (TM) and a hydroxyl equivalent mole ratio of 33:67 triethanolamine (TEA) to N,N,N',N'-tetrakis (2-hydroxypropyl) ethylenediamine (HPED). The cured forms were cut with a resistive wire cutter into 50×50×25 mm blocks and washed to remove residual surfactants and catalysts. The previously reported cleaning protocol involved two, 15 minute sonication intervals in reverse osmosis (RO) water, one interval in a 20 vol % Contrad® 70 solution in RO water (Decon Laboratories, King of Prussia, Pa.), and four, 15 minute intervals in RO water. Cleaned samples were frozen in aluminum trays and lyophilized for 3 days. Dried forms were stored in polypropylene bags under desiccation.

Type IV SMP foam dog bones with thicknesses between 3-4 mm were prepared from bulk form using a resistive wire cutter and mechanical punch. Wooden blocks were adhered to each end using epoxy to mitigate sample deformation in the tensile tester grips.

Neat SMP films were prepared with the same monomer ratios as the form. The monomers were massed into a Flacktek speed mixing cup (Flacktek SpeedMixers, Landrum, S.C.) in a moisture controlled glovebox. The reaction components were then mixed at 3400 rpm for 2 minutes to create a single phase solution. Once mixed, the solution was poured into a polypropylene casting tray and oven cured by heating to 120° C. at a rate of 30° C. hr-1 and holding at 120° C. for one hour. Films were then cooled to ambient temperature, milled on a single side to a uniform thickness of 0.2 cm, and CO2 laser-cut into 2 cm squares. The top face of the film that was in contact with air during curing was preserved for surface analysis. Cured films were stored in polypropylene bags under desiccation.

Plasma Reticulation

Plasma treatment was conducted using an Aurora 0350 Plasma Surface Treatment System (Plasma Technology Systems). Polymer form blocks were fixed on a 12.5 cm tall aluminum mesh fixture centered on the back third of the reaction chamber. Polymer films were fixed to a 4.5 cm tall glass cuvette during treatment. Form dog bones were taped to bridge two 4.5 cm tall glass cuvettes during treatment. The chamber was evacuated to a base pressure of 10 mTorr, and then O2 and CF4 process gasses were introduced into the chamber at 200 sccm and 800 sccm, respectively, to bring the chamber to a pressure of 385 mtorr. Block form samples were plasma treated at 300 Watts for 8 or 15 minutes for partial or full reticulation, respectively. Form dog bones were plasma treated at 300 Watts for 1, 2, and 3 minutes to achieve increasing degrees of reticulation, with 3 minutes achieving full reticulation. Unless otherwise stated, all film samples were plasma treated with a 15 minute process. All plasma-treated samples were stored in polyethylene bags under desiccation.

Scanning Electron Microscopy

Using a resistive wire cutter, form samples were cut into 1 mm slices parallel (axial) and orthogonal (transverse) to the forming axis. Each slice was mounted to a stage with carbon black tape and sputter coated for 90 seconds at 20 mA using a Cressington Sputter Coater (Ted Pella, Inc. Redding, Calif.). Samples were then visualized using a Joel NeoScope JCM-5000 Scanning Electron Microscope (SEM) (Nikon Instruments, Inc., Melville, N.Y.).

Permeability

The porous media properties of the plasma-reticulated and untreated forms were measured using a permeability system as previously reported and calculated using the Forchheimer-Hazen-Dupuit-Darcy (FHDD) equation (1):

$$-\partial P/\partial x = \mu/K v\_0 + \rho C v\_0^2 \quad (1)$$

where, $\partial P/\partial x$ is the pressure gradient across the sample in the direction of flow (Pa m-1), $\mu$ is the dynamic viscosity of the working fluid (Pa·s), K is the permeability of the sample (m2), $v\_0$ is the Darcy velocity (flow rate divided by the cross-sectional area of the sample) (m s-1), p is the density of the fluid (kg m-3), and C is the form factor of the sample (m-1). Permeability, K, and form factor, C, are geometric parameters of the form.

Permeability test samples (untreated, partially reticulated, and fully reticulated foams) were cut into 16×20 mm (OD× length) cylinders using a resistive wire cutter and biopsy punch. Each sample was slightly compressed to fit into a 30×19×16 mm (length×OD×ID) poly(methyl methacrylate) (PMMA) tube. UV cure epoxy (Dymax See-Cure 1202-M-SC, Dymax Corporation, Torrington, Conn.) was applied to the exterior surface of each cylindrical sample using a plastic spatula. Each sample was then placed into the PMMA tube with one end of the cylindrical sample flush with the tube opening. The epoxy was UV cured for 30 sec (OmniCure® S1000, Lumen Dynamics, Canada) to bond the form to the tube, and samples were stored under desiccation until testing.

Prior to permeability testing, each sample was sonicated in water for 1 hr to remove air bubbles. The pressure drop across each form sample was measured for at least 30 seconds at flow rates ranging from 0 to 750 mL min-1 (0 to 0.065 m s-1 Darcy velocity) to determine the K and C values of the form. Each sample was initially measured with two digital 206,800 Pa pressure gauges (model #DPGWB-06, Dwyer Instruments, Michigan City, Ind.) to determine the peak pressure at maximum flow rate and to select the highest resolution transducer for subsequent tests. Based on these results, untreated and partially reticulated samples were analyzed using two 206,800 Pa absolute membrane pressure transducers (model #PX42G7-030GV, Omega Engineering, Inc.). Fully reticulated samples were analyzed using 2,482 Pa (model #PX409-10WDWUV, Omega Engineering, Inc) and 17,240 Pa (model #PX409-2.5DWUV, Omega Engineering, Inc.) differential pressure transducers.

A second-order least squares fit was applied to the pressure gradient versus Darcy velocity data to calculate K and C for each sample using Equation 1 with water at room temperature as the working fluid.

Tensile Testing

Uniaxial tensile tests were conducted at room temperature using an Insight 30 Material Tester (MTS Systems Corporation, Eden Prairie, Minn.) with a constant strain rate of 50 mm/min. Ultimate tensile strength (kPa), strain at break (%), and elastic modulus (kPa) were calculated from the stress-strain curve of each sample.

Volumetric Expansion

Three cylindrical samples measuring 6×5 mm (OD× length) were prepared for each reticulation condition using a biopsy punch and razor blade. The form samples were threaded axially onto a 200 micron diameter nitinol wire (NDC, Fremont, Calif.) and loaded into a SC150 Stent Crimper (Machine Solutions, Flagstaff, Ariz.) preheated to 100° C. The samples were equilibrated for 15 min before being radially compressed. The samples remained constrained until they were cooled back to room temperature. Crimped form over wire samples were stored under desiccation for a minimum of 24 hours before expansion testing. Samples were mounted within a custom aluminum fixture that held the samples in the same imaging plane as a 12 mm measuring reference. The fixture was submerged in a 37° C. water bath and imaged at 1 minute intervals for 15 minutes. Five diameter measurements were made along the length of each sample at each time point using ImageJ analysis software (National Institute of Health, MD, USA).

Static Water Contact Angle

Static water contact angle measurements were made on untreated and plasma treated films (300 Watts for 15 minutes) using a CAM 200 Goniometer (KSV Instruments) and drop volumes of 5 µl. Contact angles were measured at day 0, 7, 14, 21, and 28 post reticulation to examine hydrophobic relaxation of the sample. Three contact angles were measured using a Young/Laplace fitting model on 4 separate films for a total of 12 measurements for each process and time point.

Platelet Attachment

Bovine blood was acquired from a slaughterhouse immediately following animal sacrifice. To prevent coagulation, the blood was citrated in a 1 L glass jar with a 9:1 volume ratio of blood to 3.2% sodium citrate solution in phosphate buffered saline (PBS, pH 7.4). All blood studies were completed within 8 hours of animal sacrifice.

Plasma treated (1 and 28 days post-treatment) and untreated films were rinsed three times with PBS and placed in a petri dish with the plasma-treated surface face up. The samples were submerged in citrated whole bovine blood and incubated for 1 hour at 37° C. After removing blood from the petri dish, the samples were rinsed three times with PBS and fixed with 3.7% glutaraldehyde at 37° C. for two hours. A total of 16 images were captured for each sample surface condition using a brightfield microscope (Nikon Eclipse TE2000-S) at 40× magnification. Platelets were manually counted within each field of view, and platelet attachment density was calculated using known objective scaling.

Cell Culture

Cell-material interactions were evaluated on plasma treated (0 and 28 days post treatment) and untreated films. Films (n=3 per treatment condition) were sterilized under UV light for three hours prior to seeding green fluorescent protein (GFP)-expressing 3T3 fibroblasts (NIH3T3/GFP, Cell Biolabs Inc., USA) on their surfaces at 200 cells mm-2. At set time points (3 hr, 1, 3, and 7 days), cells were imaged using fluorescent microscopy (excitation: 488 nm, Nikon FN1 Upright Microscope, NY, USA). Cell area was quantified using ImageJ software over three images for each film condition with five representative cells measured per image. Cell proliferation was quantified over three images for each film condition using particle analysis in ImageJ with manual verification.

Results

Influence of Form Morphology on Fluid Permeability

Figure 6A:
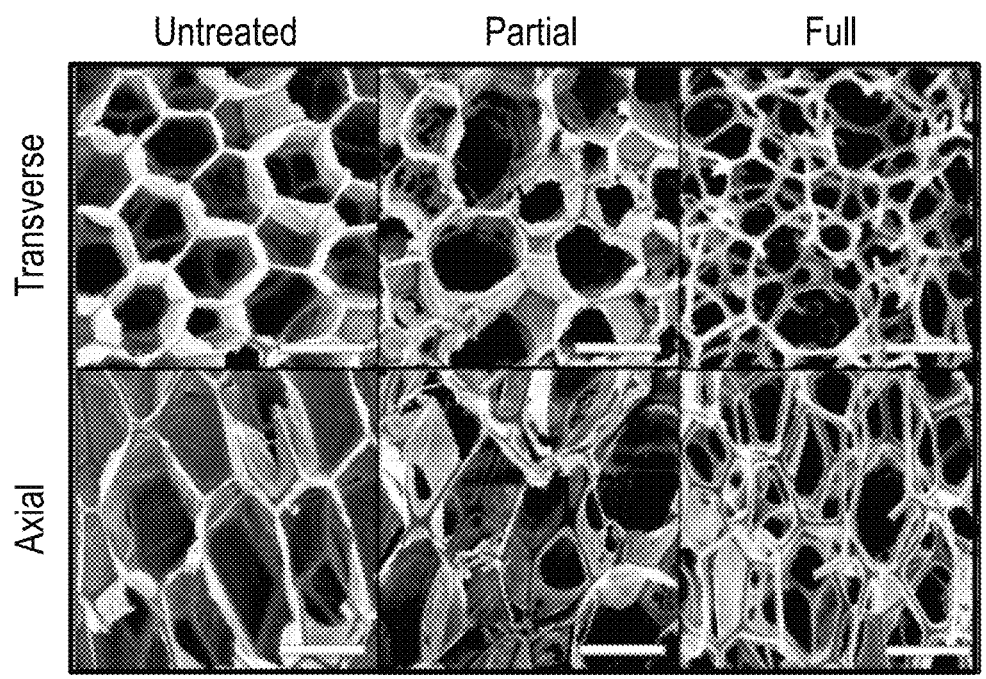
FIG. 6A depicts varying levels of reticulation in embodiments and FIG. 6B addresses form permeability for various embodiments.

The plasma-induced changes in form morphology are clearly visualized via SEM imaging, FIG. 6A. Untreated forms have inter-pore membranes that are still largely intact. The partially reticulated foams have moderate membrane degradation with pinholes in the majority of the membranes, providing a degree of pore interconnectivity while maintaining a large surface area of membranes for blood-material interactions. Only a small percentage of membranes remain in the fully reticulated foams, while the form struts remain intact. Full reticulation provides an open porous matrix for improved fluid permeability and cellular infiltration.

It is important to note the diffusive nature of the reticulation process. The larger form block samples exhibited a slight reticulation gradient at higher reticulation levels, with the exterior of the form being more reticulated than the center. All samples were taken from the center of SMP foam blocks where reticulation was most consistent between runs. However, the thinner dog bone samples did not exhibit this gradient effect, highlighting the need to tailor each process duration to the specific form geometry. Additional considerations for process reproducibility include starting chamber temperature, RF shielding from multiple samples, sample fixturing, sample orientation, and spatial positioning within the reaction chamber.

Figure 6B:
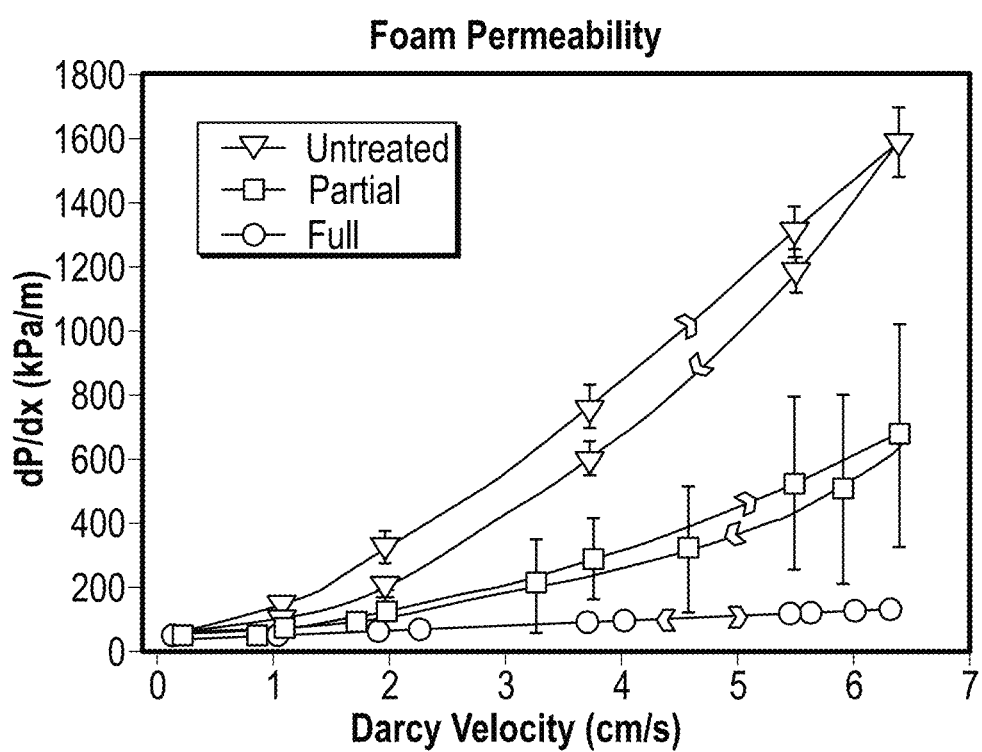

FIG. 6B quantifies the increases in material permeability due to plasma reticulation. For each reticulation condition, the permeability data is differentiated based on ramping the fluid velocity up or down to account for hysteresis. Untreated, partially reticulated, and fully reticulated foams had average form factor values of 2.91×105 m-1, 1.43×105 m-1, and 0.15×105 m-1, respectively. Average permeability values for untreated, partially reticulated, and fully reticulated foams were 0.16×10−9 m2, 1.44×10−9 m2, and 2.55× 10−9 m2, respectively. Pressure drops across fully reticulated foams are over 16 times lower than those of untreated forms at Darcy velocities (5-7 cm s-1) that correlate to those typically found in the saphenous vein (7±2 cm s-1). Partially reticulated foam permeability fell between that of untreated and fully reticulated foams, consistent with the degree of observed membrane removal. The pressure gradient standard deviations for partially reticulated foams were significantly higher than those of untreated or fully reticulated foams due to the relative inhomogeneity of the reticulation.

Influence on Mechanical Integrity

Table III summarizes the tensile mechanical properties of plasma reticulated SMP foams. Increasing reticulation resulted in moderate decreases in ultimate tensile stress and increases in strain to failure. These material properties are largely preserved because the form struts that are left intact after reticulation contribute more to the tensile integrity and overall cross sectional area of the form when compared to membranes.

TABLE III

Tensile mechanical properties of untreated and plasma reticulated foams (n = 5, average ± standard deviation)

| Plasma Duration [min] | Ultimate Stress [kPa] | Strain at Break [%] | Elastic Modulus [kPa] |
|---|---|---|---|
| 0 (Untreated) | 106 ± 7 | 38 ± 6 | 490 ± 86 |
| 1 (Partial) | 97 ± 14 | 42 ± 3 | 294 ± 62 |
| 2 (Partial) | 92 ± 6 | 46 ± 3 | 241 ± 32 |
| 3 (Full) | 79 ± 3 | 44 ± 4 | 202 ± 18 |

Significant decreases in elastic modulus were observed with increasing reticulation. Membrane removal decouples the mechanical link between adjacent form struts. This affords greater flexibility for each strut and results in an overall decrease in material stiffness. Comparable decreases in elastic modulus were also observed in mechanically reticulated SMP foams.

In Vitro Shape Recovery

Figure 7:
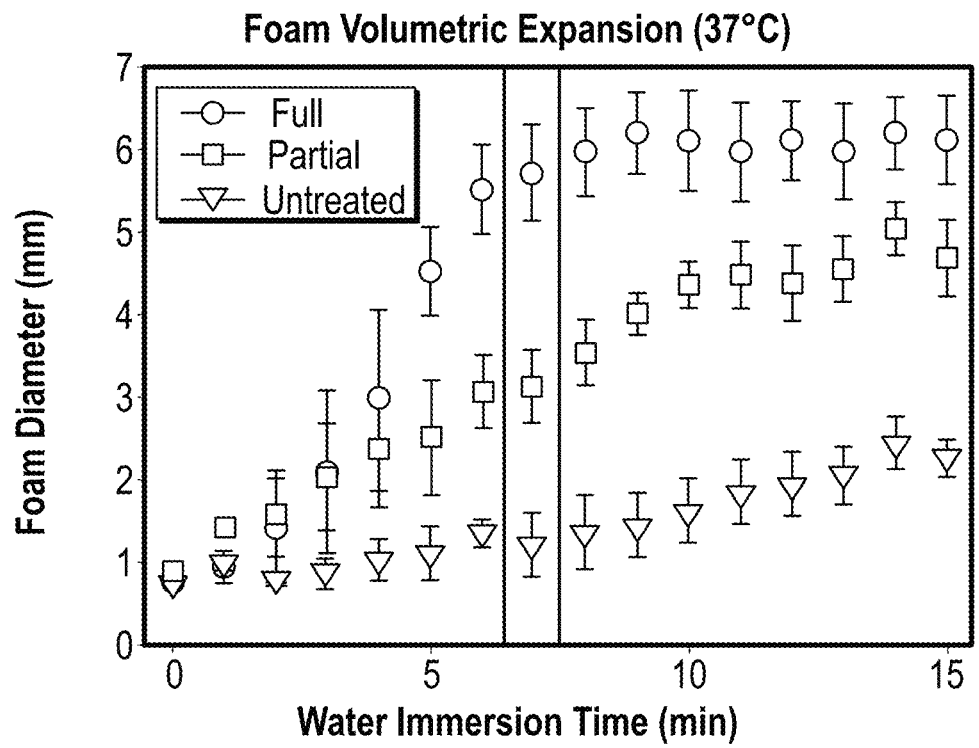
FIG. 7 addresses form volumetric expansion for embodiments.

As seen in FIG. 7, unreticulated foam samples had slow expansion rates at 37° C. with only 2 mm of expansion after 15 minutes of immersion. By comparison, partially reticulated foams expanded to almost 5 mm in diameter within 15 minutes. Fully reticulated samples achieved full shape recovery (6 mm diameter) in as little as 7 minutes.

These differences in expansion kinetics can be largely attributed to effects on moisture diffusion and moisture-plasticized glass transition temperature (Tg) depression. Actuation of SMP foams via plasticization is a known mechanism. Increased permeability from membrane removal and increased surface hydrophilicity result in faster moisture diffusion throughout the material and a more rapid decrease in Tg, increasing the expansion rate at isothermal body conditions. These changes must be considered during device development to prevent premature form expansion and excessive device friction within the delivery catheter.

Time-Dependent Surface Hydrophobicity and Thrombogenicity

Figure 8:
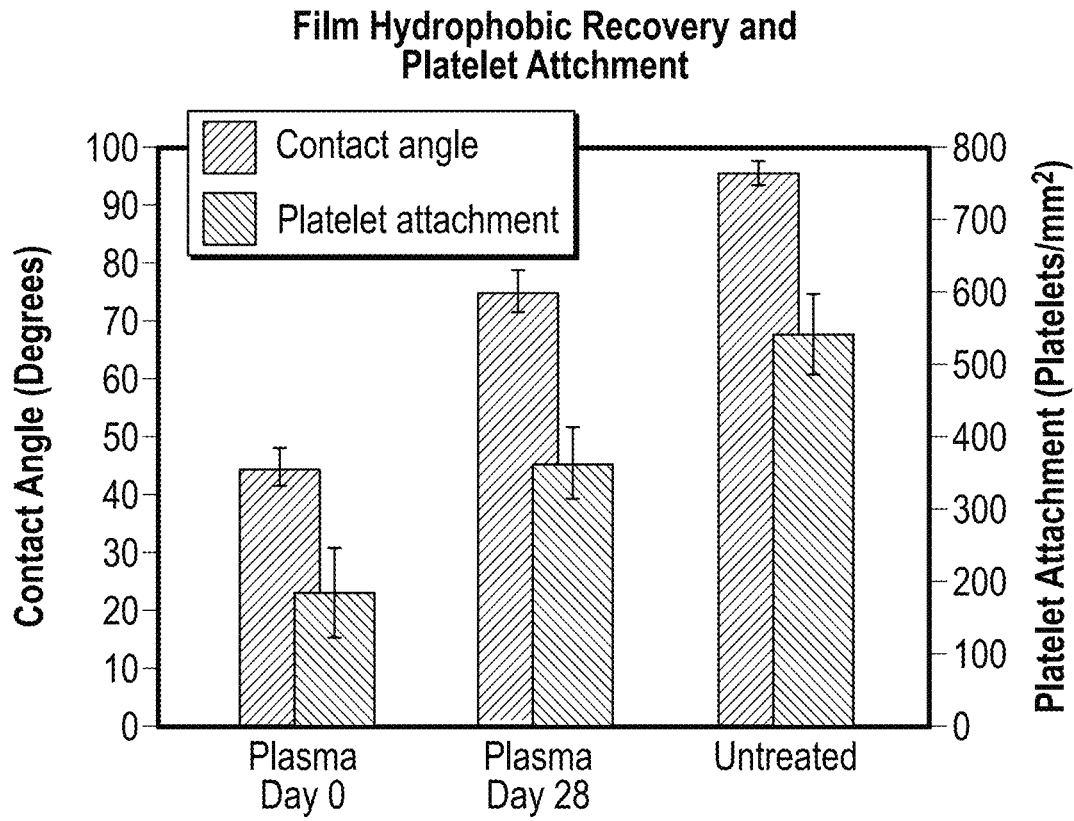
FIG. 8 addresses film hydrophobic recovery and platelet attachment in embodiments.

Contact angle measurements were made on plasma treated films to confirm the hypothesis that increased surface hydrophilicity was a driver for increased expansion rates, FIG. 8. On the day of plasma treatment, films were more hydrophilic with a contact angle of 45±3° compared to untreated films with a contact angle of 96±2°. However, the plasma treated surfaces exhibited hydrophobic recovery with an increased contact angle of 75±4° after four weeks of storage in desiccated air.

Platelet attachment provides an indication of material thrombogenicity. As seen in FIG. 8, platelet attachment correlated with increased surface hydrophobicity, with higher platelet attachment to 4 week aged films than to freshly plasma treated films. This result suggests that plasma treated devices intended for embolic applications should be aged prior to delivery to maximize their thrombogenicity.

Time-Dependent Cell Responses

Figure 9A:
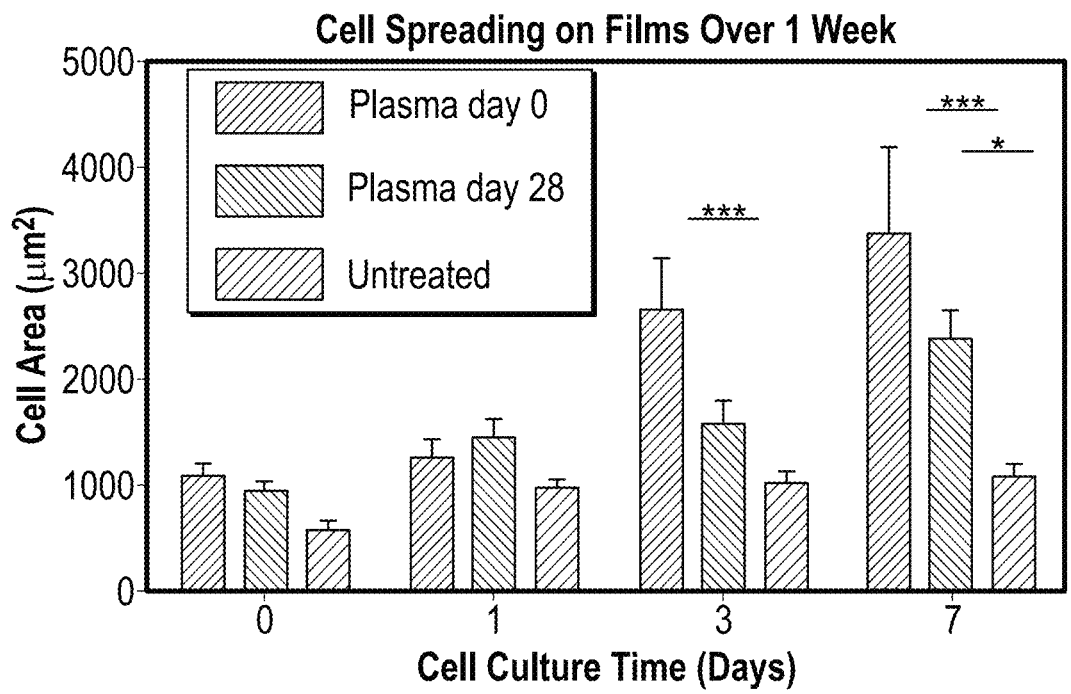
FIG. 9a addresses cell spreading on films over 1 week (area) for embodiments and FIG. 9b addresses cell spreading on films over 1 week (density) for embodiments.

Based on cell spreading morphology, cellular affinity to the plasma treated surface is demonstrated in as little as 3 hours after seeding. This initial adhesion enables significantly enhanced cell spreading on the plasma treated substrate at later time points, as seen after a week in vitro. As indicated by FIG. 9A, the cells on the control film reach a threshold of cell area at ~1 day of culture; however, cells on the plasma treated surface demonstrate highly extended pseudopodia with consistent increases in cell spreading over a week of culture. Similar fibroblast spreading behavior has been reported for tissue culture polystyrene with a comparable range of surface contact angles 63-68°. The observed decrease in cell spreading after 4 weeks post reticulation is attributed to the temporal hydrophobic recovery of the surface, FIG. 8.

Figure 9B:
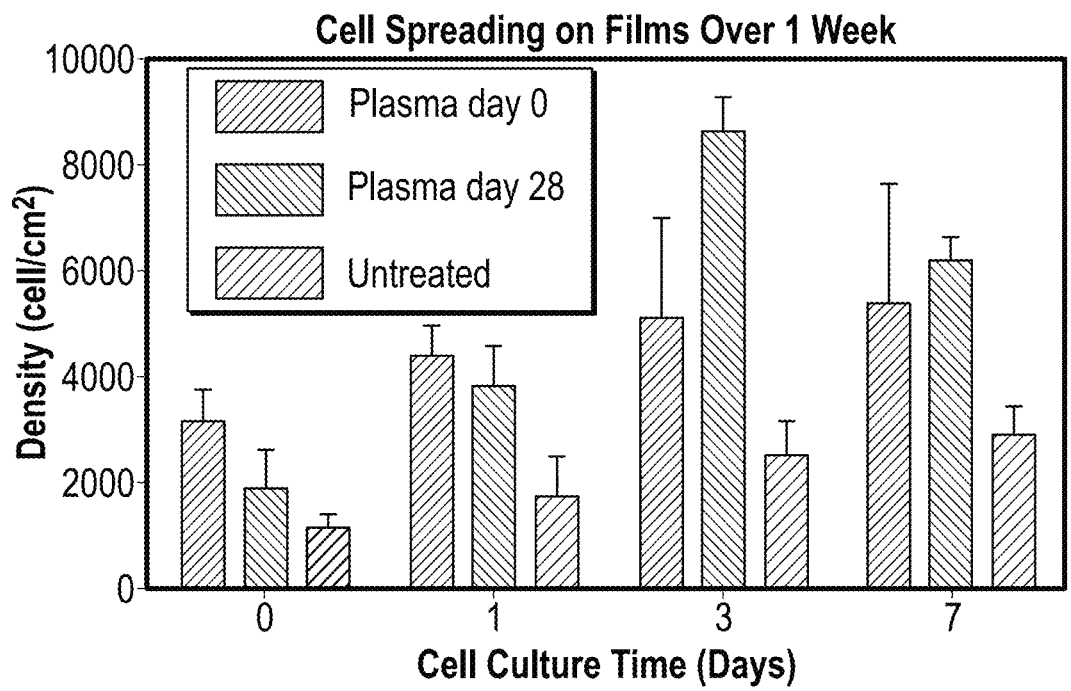

When compared to the untreated films, both plasma treated film conditions demonstrated higher cell densities, especially at the later culture time points of 3 and 7 days, FIG. 9B. Temporal changes in surface hydrophobicity did not have a significant effect on cell proliferation. Future work should characterize other potential factors contributing to these cellular responses, including surface topography. The apparent surface affinity of the plasma treated film and interconnected porous morphology of the reticulated foam indicate the promise of these materials as embolic tissue scaffolds.

The following examples pertain to further embodiments.

Example 1 includes a system comprising: a monolithic shape memory polymer (SMP) foam having first and second states; wherein the SMP foam includes: (a) polyurethane, (b) an inner half portion having inner reticulated cells defined by inner struts, (c) an outer half portion, having outer reticulated cells defined by outer struts, surrounding the inner portion in a plane that provides a cross-section of the SMP foam, (d) hydroxyl groups chemically bound to outer surfaces of both the inner and outer struts.

Another version of Example 1 includes a system comprising: a monolithic shape memory polymer (SMP) foam having first and second states; wherein the SMP foam includes: (a) polyurethane, (b) an inner half portion having inner reticulated cells defined by inner struts, and (c) an outer half portion, having outer reticulated cells defined by outer struts, surrounding the inner portion in a plane that provides a cross-section of the SMP foam.

For instance, a single piece of form may be formed or configured as a sphere, brick, or cylinder. For the cylinder, as an example, a middle or center portion (inner portion) may be surrounded by another portion (outer concentric portion) in a plane that is orthogonal to a long axis of the cylinder. Thus, the outer portion may not surround the inner portion at proximal and distal ends of the form (at opposite ends of the long axis). The portions are "half" portions to basically provide a frame of reference. Thus, for the aforementioned plane the middle half of form on the plane is the inner half and the rest of the form intersecting the plane is the outer half. Surface oxidation from the plasma reticulation process may chemically alter the surface, for example, increasing surface hydroxyl groups. The hydroxyl groups are merely on the surface of the struts (and potentially some membranes that were not completely reticulated) and do not refer to the bulk form (i.e., the actual composition of the strut itself, which may include TEA, HDI, and the like).

While polyurethane examples are mentioned herein, other types of forms may be used including, for example and without limitation, polycarbonate, polyamide, polyurea, polyester, polycaprolactone, polyolefin, or combinations thereof.

Example 2 includes the system of example 1 including a reticulation gradient such that the outer reticulated cells are more reticulated than the inner reticulated cells.

The hydroxyl groups may not be distributed evenly but may be more prevalent along outer portions of the form than inner portions of the form. This may also be indicative of spatially controlled reticulation (i.e., reticulation gradient) whereby a form (e.g., monolithic form) has varying areas of reticulation.

Example 3 includes the system of example 1, wherein: the SMP foam includes distal and proximal portions; the distal portion includes the inner half portion and the outer half portion; and one of the distal and proximal portions includes cells that are more heavily reticulated than another of the distal and proximal portions.

Thus, the gradient is not necessarily inside/outside as in Example 2 but may instead be in different portions of the form due to masking and the like. For example, a mask placed over a distal part of a form cylinder will hinder reticulation in that area vs. an unmasked proximal part of the form. The gradient may be immediate or gradual.

Example 4 includes the system of example 1, wherein the SMP foam has a surface energy configured to recover towards increasing hydrophobicity over time based on changes in surface chemistry.

Another version of Example 4 includes the system of example 1, wherein the SMP foam has a surface energy configured to recover towards increasing hydrophobicity over time (e.g., 2 months after plasma reticulation of the form).

Another version of Example 4 includes the system of example 1, wherein the SMP foam has a surface energy configured to recover towards increasing hydrophobicity.

For example, oxygen containing functional groups may preferentially reorient into (towards the center) the bulk material in time (e.g., several weeks depending on the atmosphere in which the form is stored/packaged), leading to a temporal increase in hydrophobicity.

Example 5 includes the system of example 1, wherein the inner and outer struts both include N,N,N',N'-tetrakis (2-hydroxypropyl) ethylenediamine (HPED), triethanolamine (TEA), and hexamethylene diisocyanate (HDI) and more TEA than HPED.

Another version of Example 5 includes the system of example 1, wherein the inner and outer struts both include N,N,N',N'-tetrakis (2-hydroxypropyl) ethylenediamine (HPED), triethanolamine (TEA), and hexamethylene diisocyanate (HDI) with TEA contributing a higher molar ratio of hydroxyl groups than HPED.

Example 6 includes the system of example 5, wherein the SMP foam has a density less than 0.06 g/cm$^3$.

Other embodiments include a density less than 0.04, 0.08, 0.1, and 0.5 g/cm$^3$.

Example 7 includes the system of example 1, wherein the inner and outer struts both include N,N,N',N'-tetrakis (2-hydroxypropyl) ethylenediamine (HPED), triethanolamine (TEA), and trimethylhexamethylenediamine (TMHDI) and more HPED than TEA.

Another version of example 7 includes the system of example 1, wherein the inner and outer struts both include N,N,N',N'-tetrakis (2-hydroxypropyl) ethylenediamine (HPED), triethanolamine (TEA), and trimethylhexamethylenediamine (TMHDI) with HPED contributing a higher molar ratio of hydroxyl groups than TEA.

Example 8 includes the system of example 1 comprising a hydrocarbon film, wherein: the SMP foam includes additional inner struts and additional outer struts, surrounding the inner portion in a plane that provides a cross-section of the SMP foam; and the hydrocarbon film covers both of the additional inner struts and the additional outer struts.

Thus, in an embodiment some struts may include hydroxyl groups from a plasma reticulation process while other different struts may by covered by the hydrocarbon film. Some struts may include both hydroxyl groups and the film. In such an example, the surface hydrocarbon film may override the OH groups (if film is formed after reticulation). The OH groups may quickly reorient at the interface with the film (thereby removing or lessening a need to let surface energy recover towards increasing hydrophobicity as described above with regard to Example 4). In some embodiments the reticulation process occurs and then the material is aged (e.g., 1, 2, 3, 4 weeks or more) to allow the material surface to recover to its inherent state. The hydrocarbon film may or may not then be applied.

The form of Example 8 may have inner and outer struts that both include N,N,N',N'-tetrakis (2-hydroxypropyl) ethylenediamine (HPED), triethanolamine (TEA), and hexamethylene diisocyanate (HDI) with TEA contributing a higher molar ratio of hydroxyl groups than HPED.

The form of Example 8 may have inner and outer struts that both include N,N,N',N'-tetrakis (2-hydroxypropyl) ethylenediamine (HPED), triethanolamine (TEA), and trimethylhexamethylenediamine (TMHDI) with HPED contributing a higher molar ratio of hydroxyl groups than TEA.

By altering the bulk hydrophobicity of the form (i.e., changing chemistry within the strut itself such as HPED contributing a higher molar ratio of hydroxyl groups than TEA or TEA contributing a higher molar ratio of hydroxyl groups than HPED) and the diffusion characteristics of the surface (not within the strut but the surface of the strut), the actuation profile of the form can be tailored for delayed expansion in body temperature water Another version of Example 8 includes wherein the inner and outer struts both include N,N,N',N'-tetrakis (2-hydroxypropyl) ethylenediamine (HPED), Glycerol, pentanediol, and hexamethylene diisocyanate (HDI).

Example 9 includes the system of example 8, wherein the hydrocarbon film is no thicker than 500 nm.

However, in other embodiments the film is no thicker than 100, 200, 300, or 400 nm.

Example 10 includes the system of example 8, wherein the hydrocarbon film is hydrophobic.

Example 11 includes the system of example 8, wherein the additional inner struts are included in the inner half portion and the additional outer struts are included in the outer half portion.

Example 12 includes the system of example 8, wherein the hydrocarbon film includes a hydrocarbon polymer that further includes vinyl groups.

Example 13 includes the system of example 8, wherein the SMP foam includes a non-linear expansion rate when exposed to thermal stimulus based on the hydrocarbon film.

For example, upon exposure to thermal stimulus (or other forms of stimulus in other embodiments such as magnetic radiation, light, change in pH, and the like) and moisture (e.g., water component of blood) expansion or return to programmed shape may occur. This may occur at a non-linear rate due to delay caused by the hydrocarbon film. As moisture eventually progresses towards the center of the form expansion rate may increase due to plasticization and consequent Tg depression. This may be especially true for forms that have less of the hydrocarbon film on their inner struts than on their outer struts. In such a case, water diffusion would progress more rapidly after an initial delay. This provides preferred working time for those handling the forms, such as physicians deploying the forms within a patient.

In an embodiment the hydrocarbon coating coats the individual struts and may form a monolithic film that extends from an outer strut to an inner strut. Such a film may not extend along the outside of the form like some form of sleeve or outer conduit that extends across cells. Instead, by providing a thin nanolayer (e.g., less than 50, 100, 150, 200, 250, 300 nm or more) a low density form may still be able to expand without mechanical constraint from a thick diffusion layer (e.g., hydrophobic diffusion barrier).

Example 14 includes a system comprising: a monolithic shape memory polymer (SMP) foam having first and second states; and a hydrocarbon film; wherein the SMP foam includes: (a) polyurethane, (b) an inner half portion having inner reticulated cells defined by inner struts, and (c) an outer half portion, having outer reticulated cells defined by outer struts, surrounding the inner portion in a plane that provides a cross-section of the SMP foam; wherein the hydrocarbon film covers both of the inner and outer struts.

Example 15 includes the system of example 14, wherein the hydrocarbon film is no thicker than 500 nm and the hydrocarbon film is hydrophobic.

Example 16 includes a method comprising: locating a monolithic shape memory polymer (SMP) foam having first and second states in a plasma chamber; evacuating the chamber to a first pressure level range; providing a first gas to the chamber while at the first pressure level range; ionizing the first gas into a first plasma; exposing the SMP foam to the first plasma for a first period of time to reticulate cells of the SMP foam and oxidize both the inner and outer strut surfaces; and exposing the SMP foam to atmospheric pressure; wherein the SMP foam includes: (a) polyurethane, (b) an inner half portion having inner reticulated cells defined by inner struts, and (c) an outer half portion, having outer reticulated cells defined by outer struts, surrounding the inner portion in a plane that provides a cross-section of the SMP foam.

Figure 10:
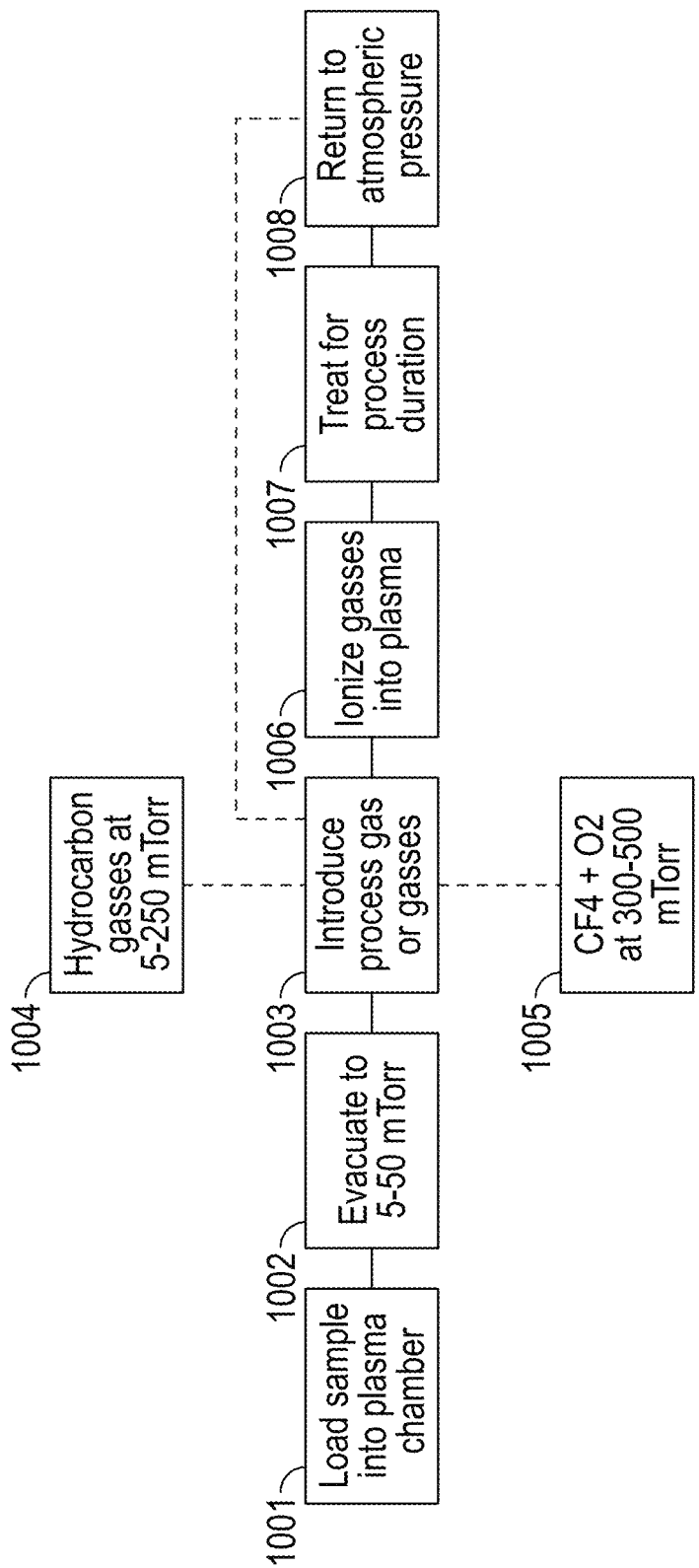
FIG. 10 includes a process or processes in an embodiment.

For example, in FIG. 10 block 1001 includes locating a monolithic shape memory polymer (SMP) foam having first and second states in a plasma chamber. Block 1002 includes evacuating the chamber to a first pressure level range. Block 1003 includes providing a first gas to the chamber while at the first pressure level range. This may include either the step of block 1004 or 1005. In other words, in one embodiment introducing the process gas or gasses includes introducing hydrocarbon gases at a pressure range (block 1004) if a diffusion barrier is the process goal. This may then be followed by ionizing those gases into a plasma (block 1006), treating the form with the plasma (which would include functionalizing the form surface with a hydrocarbon film if block 1004 is included) (block 1007), and then returning the chamber to atmospheric pressure (block 1008).

Another embodiment includes introducing the process gas or gasses which includes introducing oxygen and tetrafluoromethane at a pressure range (block 1005) if plasma reticulation is the process goal. This may then be followed by ionizing those gases into a plasma (block 1006), treating the form with the plasma (which would include functionalizing the form surface with hydroxyl groups if block 1005 is included) (block 1007), and then returning the chamber to atmospheric pressure (block 1008).

Another embodiment may include following one procedure with another via step 1009. For example, reticulation (block 1005) may be performed first (along with a first pass at blocks 1006, 1007, 1008) followed by the addition of a diffusion barrier (block 1004) (along with a second pass at blocks 1006, 1007, 1008). The barrier addition may follow the reticulation process almost immediately or after several weeks or more (which may be implemented to allow surface energy reconfiguration as addressed in Example 4). With such a delay, the reticulation may occur in one chamber with the barrier addition occurring in another chamber or the same chamber as the reticulation.

Certainly reticulation and hydrocarbon diffusion barriers may each be implemented independently of each other.

The process time of block 1007 may lead to a gradient. For example, a shorter time may lead to greater reticulation and/or barrier on the outer portions of the form than is present on inner portions of the form (because the plasma has less time to access inner portions of the form).

The form may be treated in a large block or already formed into its end form (e.g., an aneurysm plug or a liner for a helmet).

Example 17 includes the method of example 16 comprising, after exposing the SMP foam to the first plasma for a first period of time, the following: evacuating at least one of the chamber and another chamber, which includes the SMP foam, to a second pressure level range; providing a second gas to the at least one of the chamber and another chamber while at the second pressure level range; ionizing the second gas into a second plasma; and exposing the SMP foam to the second plasma for a second period of time to form a hydrocarbon film on the outer surfaces of both the inner and outer struts; wherein the hydrocarbon film is no thicker than 500 nm.

Example 18 includes the method of example 17, wherein the first gas includes oxygen and tetrafluoromethane and the second gas includes a member selected from the group consisting of acetylene, ethylene, propylene, methane, isobutylene, ethane, propane, butane, and argon.

Example 19 includes the method of example 17 including masking a portion of the SMP foam before exposing the SMP foam to the second plasma for the second period of time.

The masking may occur before the form is located in the chamber to thereby form a barrier change whereby one part of the form has more of the barrier than another part of the form.

Example 20 includes the method of example 16 including masking a portion of the SMP foam before exposing the SMP foam to the first plasma for the first period of time.

The masking may occur before the form is located in the chamber to thereby form a reticulation change whereby one part of the form has more reticulation than another part of the form.

Example 1a includes a process for the modification of the surface of a polymer form, the process comprising modifying the surface of the polymer using plasma, to achieve control over the spatial variation, or to introduce a gradient in the degree of functionalization of the form.

Example 2a includes the process of example 1a, wherein the modification of the surface of the form comprises oxidation of the surface.

Example 3a includes the process of example 1a, wherein the modification of the surface of the form comprises functionalization of the surface.

Example 4a includes the process of example 3a, wherein the functionalization is passive.

Example 5a includes the process of example 4a, wherein the passive functionalization changes the surface behavior of the material and the manner in which it reacts with the environment.

Example 6a includes the process of example 3a, wherein the functionalization is semi-active.

Example 7a includes the process of example 6a, wherein the semi-active functionalization causes the form surface to actively interact with the surrounding media.

Example 8a includes the process of example 3a, wherein the functionalization is active.

Example 9a includes the process of example 8a, wherein the active functionalization causes the form surface to actively interact with the surrounding media, leading to a subsequent change in its own behavior.

Example 10a includes a process for the sterilization of a surface, the process comprising introducing plasma on the surface requiring to be sterilized.

Example 11a includes a process of example 10a, wherein the surface film is deposited using a PECVD technique.

Example 12a includes the process of example 1a, wherein the polymer form is a shape memory form.

Example 1b includes a method comprising: locating a monolithic shape memory polymer (SMP) foam having first and second states in a plasma chamber; evacuating the chamber to a first pressure level range; providing a first gas mixture to the chamber while at the first pressure level range; ionizing the first gas mixture into a first plasma; exposing the SMP foam to the first plasma for a first period of time to reticulate cells of the SMP foam and oxidize surfaces of inner and outer struts of the reticulated cells; and exposing the SMP foam to atmospheric pressure; wherein the SMP foam includes (a) polyurethane, (b) an inner half portion including the inner struts, and (c) an outer half portion, including the outer struts, surrounding the inner portion in a plane that provides a cross-section of the SMP foam.

Example 2b includes the method of example 1b comprising, after exposing the SMP foam to the first plasma, the following: evacuating at least one of the chamber and another chamber, which includes the SMP foam, to a second pressure level range; providing a second gas mixture to the at least one of the chamber and another chamber while at the second pressure level range; ionizing the second gas mixture into a second plasma; and exposing the SMP foam to the second plasma for a second period of time to form a hydrocarbon film on the oxidized surfaces of both the inner and outer struts; wherein the hydrocarbon film is no thicker than 500 nm.

Example 3b includes the method of example 2b, wherein the first gas mixture includes oxygen and tetrafluoromethane and the second gas mixture includes at least one member selected from the group consisting of acetylene, ethylene, propylene, methane, isobutylene, ethane, propane, butane, and argon.

Example 4b includes the method of example 2b including masking a portion of the SMP foam before exposing the SMP foam to the second plasma for the second period of time.

Example 5b includes the method of example 1b including masking a portion of the SMP foam before exposing the SMP foam to the first plasma for the first period of time.

The foregoing description of the embodiments has been presented for the purposes of illustration and description. It is not intended to be exhaustive or to limit the embodiments to the precise forms disclosed. This description and the claims following include terms, such as left, right, top, bottom, over, under, upper, lower, first, second, etc. that are used for descriptive purposes only and are not to be construed as limiting. The embodiments of a device or article described herein can be manufactured, used, or shipped in a number of positions and orientations. Persons skilled in the relevant art can appreciate that many modifications and variations are possible in light of the above teaching. Persons skilled in the art will recognize various equivalent combinations and substitutions for various components shown in the Figures. It is therefore intended that the scope of the embodiments be limited not by this detailed description, but rather by the claims appended hereto.

What is claimed is:

1. A shape memory polymer system comprising:
a monolithic shape memory polymer (SMP) foam having first and second states; and
a hydrocarbon film;
wherein the SMP foam is a tissue scaffold and includes: (a) polyurethane, (b) an inner half portion having inner reticulated cells defined by inner struts, and (c) an outer half portion, having outer reticulated cells defined by outer struts, surrounding the inner half portion in a plane that provides a cross-section of the SMP foam;
wherein: (a) the hydrocarbon film directly contacts both of the inner struts and the outer struts, and (b) the SMP foam includes a non-linear expansion rate when exposed to thermal stimulus based on the hydrocarbon film.

2. The system of claim 1 including a reticulation gradient such that the outer reticulated cells are more reticulated than the inner reticulated cells.

3. The system of claim 1, wherein:
the SMP foam includes distal and proximal portions;
the distal portion includes the inner half portion and the outer half portion; and one of the distal and proximal portions includes cells that are more heavily reticulated than another of the distal and proximal portions.

4. The system of claim 1, wherein the SMP foam has a surface energy configured to recover towards increasing hydrophobicity over time.

5. The system of claim 1, wherein the inner and outer struts both include a reaction product of N,N,N',N'-tetrakis (2-hydroxypropyl) ethylenediamine (HPED), triethanolamine (TEA), and hexamethylene diisocyanate (HDI).

6. The system of claim 1, wherein the inner and outer struts both include a reaction product of N,N,N',N'-tetrakis (2-hydroxypropyl) ethylenediamine (HPED), triethanolamine (TEA), and trimethyl hexamethylene diisocyanate (TMHDI).

7. The system of claim 1, wherein the hydrocarbon film is hydrophobic and is no thicker than 500 nm.

8. The system of claim 1, wherein the hydrocarbon film is hydrophobic.

9. The system of claim 1, wherein the SMP foam includes hydroxyl groups chemically bound to outer surfaces of both the inner and outer struts.

10. The system of claim 1, wherein the hydrocarbon film includes vinyl groups.

11. A shape memory polymer system comprising:
a monolithic shape memory polymer (SMP) foam having first and second states; and
a monolithic hydrocarbon film on the SMP foam;
wherein the SMP foam is a tissue scaffold and includes: (a) polyurethane, (b) an inner half portion having inner reticulated cells defined by inner struts, and (c) an outer half portion, having outer reticulated cells defined by outer struts, surrounding the inner half portion in a plane that provides a cross-section of the SMP foam;
wherein the SMP foam includes a non-linear expansion rate when exposed to thermal stimulus based on to both: (a) the hydrocarbon film being configured to induce a change to a rate of moisture plasticization of the SMP foam, and (b) the inner struts having less of the hydrocarbon film than the outer struts.

12. The system of claim 11, wherein the hydrocarbon film includes only hydrogen and carbon and is no thicker than 50 nm and the hydrocarbon film is hydrophobic.

13. A system comprising:
a monolithic shape memory polymer (SMP) foam having first and second states; and
a hydrocarbon film;
wherein the SMP foam is a tissue scaffold and includes: (a) polyurethane, (b) an inner half portion having inner non-thermal plasma-reticulated cells defined by inner form-struts, and (c) an outer half portion, having outer non-thermal plasma-reticulated cells defined by outer form-struts, surrounding the inner half portion in a plane that provides a cross-section of the SMP foam;
wherein: (a) the hydrocarbon film coats both of the inner form-struts and the outer form-struts, (b) the SMP foam includes a non-linear expansion rate when exposed to moisture due to hydrocarbon film-induced plasticization rate depression, and (c) the SMP foam is thrombogenic based on a surface-to-volume ratio of the SMP foam.

14. The system of claim 13 including a reticulation gradient such that the outer non-thermal plasma-reticulated cells are more reticulated than the inner non-thermal plasma-reticulated cells.

15. The system of claim 13, wherein both of the inner and outer form-struts: (a) include a reaction product of N,N,N', N'-tetrakis (2-hydroxypropyl) ethylenediamine (HPED), triethanolamine (TEA), and hexamethylene diisocyanate (HDI), and (b) are biodegradable.

16. The system of claim 15, wherein the SMP foam is hydrophobic and the hydrocarbon film is hydrophobic.

17. The system of claim 13, wherein both of the inner and outer form-struts: (a) include a reaction product of N,N,N', N'-tetrakis (2-hydroxypropyl) ethylenediamine (HPED), triethanolamine (TEA), and trimethyl hexamethylene diisocyanate (TMHDI), and (b) are biodegradable.

18. The system of claim 17, wherein the SMP foam is hydrophobic and the hydrocarbon film is hydrophobic.

19. The system of claim 13, wherein the SMP foam includes hydroxyl groups chemically bound to outer surfaces of both the inner and outer form-struts.

20. The system of claim 13, wherein the hydrocarbon film comprises hydrogen, carbon, and oxygen.

* * * * *

UNITED STATES PATENT AND TRADEMARK OFFICE
CERTIFICATE OF CORRECTION

PATENT NO. : 11,459,439 B2
APPLICATION NO. : 16/984370
DATED : October 4, 2022
INVENTOR(S) : Landon D. Nash et al.

It is certified that error appears in the above-identified patent and that said Letters Patent is hereby corrected as shown below:

In the Claims

Column 24:
Line 26, "form-struts" should read --foam-struts--;
Line 28, "form-struts" should read --foam-struts--;
Line 31, both occurrences, "form-struts" should read --foam-struts--;
Line 41, "form-struts" should read --foam-struts--;
Line 48, "form-struts" should read --foam-struts--;
Line 56, "form-struts" should read --foam-struts--.

Signed and Sealed this
Eighth Day of November, 2022

Katherine Kelly Vidal
*Director of the United States Patent and Trademark Office*